United States Patent
Dai et al.

(10) Patent No.: US 8,415,446 B2
(45) Date of Patent: Apr. 9, 2013

(54) CARDANOL BASED DIMERS AND USES THEREFOR

(75) Inventors: Zhisheng Dai, Cranburry, NJ (US); Adarsh Dalal, Lodi, NJ (US); Donald C. Lawson, III, Coplay, PA (US); Jinbao He, Edison, NJ (US)

(73) Assignee: Carolite Corporation, Newark, NJ (US)

( * ) Notice: Subject to any disclaimer, the term of this patent is extended or adjusted under 35 U.S.C. 154(b) by 135 days.

(21) Appl. No.: 12/948,669

(22) Filed: Nov. 17, 2010

(65) Prior Publication Data

US 2011/0065832 A1    Mar. 17, 2011

Related U.S. Application Data

(62) Division of application No. 12/114,333, filed on May 2, 2008, now Pat. No. 7,858,725.

(60) Provisional application No. 60/927,420, filed on May 3, 2007.

(51) Int. Cl.
*C08G 77/12*    (2006.01)

(52) U.S. Cl.
USPC ............................................. 528/31; 528/25

(58) Field of Classification Search ............ 528/31, 528/25
See application file for complete search history.

(56) References Cited

U.S. PATENT DOCUMENTS

| | | | |
|---|---|---|---|
| 3,931,267 A | | 1/1976 | Brode |
| 4,563,386 A | * | 1/1986 | Schwartz ................. 442/101 |
| 4,866,026 A | | 9/1989 | Henzel et al. |
| 5,204,438 A | | 4/1993 | Snow et al. |
| 5,349,102 A | | 9/1994 | Tuinstra et al. |

OTHER PUBLICATIONS

International Search Report, Sep. 3, 2008.

* cited by examiner

*Primary Examiner* — Kuo-Liang Peng
(74) *Attorney, Agent, or Firm* — McCarter & English, LLP

(57) ABSTRACT

Cardanol based dimers are provided. The cardanol dimers are formed by hydrosylylation with silanes. Cardanol based dimers may be further reacted to form epoxy curing agents and epoxies which can be used as anti-fouling coatings on ship hulls and marine structures. The cardanol dimers may also be used to produce friction particles or phenolic resins. Methods of synthesizing the cardanol based dimers, the epoxy curing agents and the epoxies are also provided.

14 Claims, 19 Drawing Sheets

CARDANOL BASED DIMERS AND USES THEREFOR

The present application is a divisional application under 35 U.S.C. §121 from U.S. application Ser. No. 12/114,333 filed on May 2, 2008, now U.S. Pat. No. 7,858,725 which claims the benefit under 35 U.S.C. §119 of U.S. Provisional Application No. 60/927,420 filed on May 3, 2007, the entire contents of each of which are hereby incorporated by reference.

FIELD OF THE INVENTION

The present invention relates, in one aspect, to dimers of cardanol formed by hydrosilylation. In another aspect, the present invention relates to the process for producing the dimers of cardanol and derivatives of those dimers. In yet another aspect, the invention relates to use of cardanol dimers to produce a self-polishing anti-fouling coating for use in marine environments.

BACKGROUND

As described in U.S. Pat. No. 6,229,054, cardanol is a meta-substituted phenol obtained by treating cashew nut shell liquid (CNSL). CNSL consists primarily of anacardic acid which is decarboxylated when heated, yielding cardanol. As shown in FIG. 1, cardanol is a phenol with a meta-substituted 15 carbon unsaturated aliphatic side chain. The aliphatic side chain may have either one, two or three carbon double bonds. Cardanol has been used as a base material to form, for example, hydroxyalkylated cardanol used as a modifier in coatings, adhesives, sealants, rubbers, plastics, elastomers and inks.

Fouling of ship bottoms and other marine structures by organisms such as barnacles, tube worms and algae is a problem which has existed from ancient times to the present. It has become routine practice to prevent these organisms from attaching to ship bottoms and other marine structures by coating exposed surfaces with an anti-fouling coating or paint.

Beginning in the mid-1800's, toxicants were included in paints for ship bottoms and other marine structures. Copper compounds, such as copper sulfate and cuprous oxide, were among the first toxicants used in anti-fouling paints. Over the years, a variety of toxicants have been used, including tin, arsenic, mercury and oxides of zinc, lead and mercury. More recently, organotins such as tributyltins, have been used in anti-fouling marine paints.

Prevention of fouling by use of toxic paints requires maintaining a lethal concentration of the toxicant in the water immediately adjacent to the surface being protected. There are at least two disadvantages to this approach: (1) the leaching action of the toxicant from the paint will eventually exhaust the supply of the toxicant and the paint will no longer be effective, and (2) the toxicants are environmentally undesirable and can be a major source of pollution in busy harbors and waterways.

One solution to these problems has been the development of so-called foulant release coatings. These coatings are often silicone based materials to which foulant organisms do not adhere. One disadvantage of these coatings is that it can be likewise difficult to adhere the material to the surface being protected. While this can sometimes be addressed in part by more extensive preparation procedures, this can increase the time and expense involved in coating a surface.

Another approach which is intended to address, at least in part, the problem of adherence of the coating to the surface is described in U.S. Pat. No. 5,593,732. This patent describes an anti-fouling coating system comprised of two layers. A solid bonding layer is bonded to the substrate, and a solid release layer is bonded to the bonding layer. This system requires multiple components and the application of two layers, increasing the time and expense associated with application of the coating.

Accordingly, there is a need for an improved anti-fouling coating which can be applied to marine structures, such as ship bottoms, economically, and that prevents marine organisms from bonding to the surface of the marine structure.

SUMMARY OF THE INVENTION

The present invention relates to dimers of cardanol formed by hydrosilylation of cardanol and processes for producing the cardanol dimers. In one embodiment, the cardanol dimers are produced by combining cardanol with tetramethyldisiloxane to produce cardanol silane dimers. In another embodiment, long chain silicone cardanol dimers are produced by combining cardanol with long chain organosilanes. In yet another embodiments, the cardanol silane dimers are further reacted with silanes to add additional silane groups on the cardanol silane dimers.

The cardanol dimers may be crosslinked by a polysilane having any desired number of silane units. Additional functional groups may also be bonded to the cardanol dimers to produce dimers having selected properties.

The present invention also relates to the use of the cardanol silane dimers to produce improved anti-fouling coatings and to methods for synthesizing the improved anti-fouling coatings. The anti-fouling coating is an epoxy-type coating. The epoxy agent and curing agents for the anti-fouling coating are produced by further processing the cardanol dimers. The resulting epoxy coating is a two component system comprising an epoxy functional resin and an amine functional curing agent both containing silicone groups.

The anti-fouling coating of the present invention exhibits a low surface energy and low coefficient of friction. The coating may be applied by brush or spray application and has excellent adhesion to metal. Standard paint pigments and extenders can be added to the coating. The epoxy has an acceptable potlife. When applied to an exposed surface such as a boat hull, the coating resists marine fouling without the use of any toxic components.

The cardanol dimers of the present invention may also be used to produce friction particles or in phenolic resins where phenol is used in an electrophilic addition reaction. Friction particles formed from the cardanol dimers of the present invention exhibit lower weight loss with heating by thermogravimetric analysis, have improved heat resistance and exhibit improved thermal shock properties.

Other advantages of the coating will be apparent to those skilled in the art based upon the following detailed description of preferred embodiments.

DETAILED DESCRIPTION OF PREFERRED EMBODIMENTS

Figure 1:
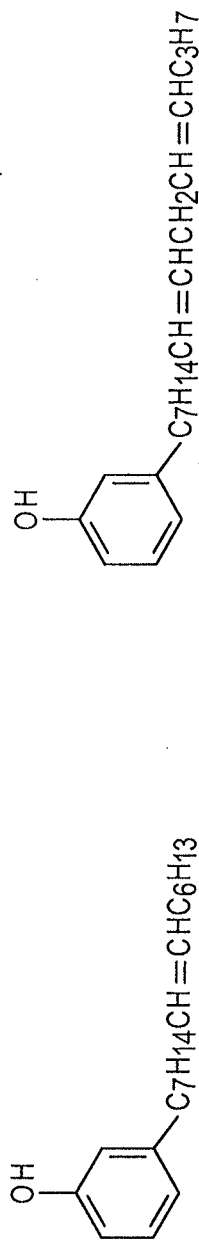
FIG. 1 is a structural diagram of cardanol.

The present invention relates to dimers of cardanol, processes for producing dimers of cardanol, and use of the dimers of cardanol in friction particles or in epoxy coatings that may be used, for example, as anti-fouling coatings on ships or marine structures. As described in U.S. Pat. No. 6,229,054, cardanol is obtained by treating cashew nut shell liquid (CNSL). CNSL consists primarily of anacardic acid which is decarboxylated when heated, yielding cardanol. As shown in FIG. 1, cardanol is a phenol with a meta-substituted 15 carbon unsaturated aliphatic side chain. The aliphatic side chain may have either one, two or three carbon double bonds. In preferred embodiments of the present invention, the unsaturated aliphatic side chain is pentadeca-8,11-diene.

The cardanol dimers of the present invention are synthesized by cross-linking the aliphatic side chains on the cardanol. In some embodiments, the aliphatic side chains are cross-linked using a multifunctional silicon molecule, such as for example a siloxane or a polysiloxane. In one embodiment, the cardanol dimers generally have the formula:

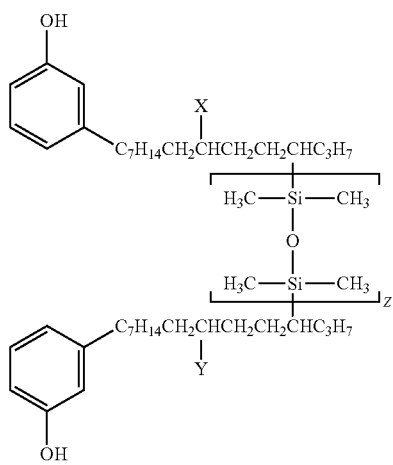

In this embodiment, z may be any desired number to obtain a cardanol dimer having the desired properties. In preferred embodiments, z is between 1 and 200, and in an especially preferred embodiment, z is 1. X and y may be the same or different species, and they may be any species that imparts desired properties on the resulting dimer. In preferred embodiments, x and y are selected from hydrogen, a halide, a hydroxyl group, a saturated or unsaturated, branched or unbranched aliphatic carbon group having between 1 and 100 carbon atoms, an aromatic carbon group, or a silane or polysilane group. The aliphatic carbon group may also be substituted at one or more carbon atoms with a hydroxyl group, a halide or any other atom or radical that can be bonded to carbon. It should be understood that, as explained for the embodiment of the dimer described below, it is not necessary to have any substitution at the $C_8$ location, and in that case the double bond between the eighth and ninth carbons on the meta-substituted side chain on the cardanol molecule is not reduced.

Alternatively, the cardanol dimer may be crosslinked at two locations on the meta-substituted side chain. In this embodiment, at the $C_9$ location on the meta-substituted side chain, a second silane or polysilane crosslink is formed to produce the following dimer:

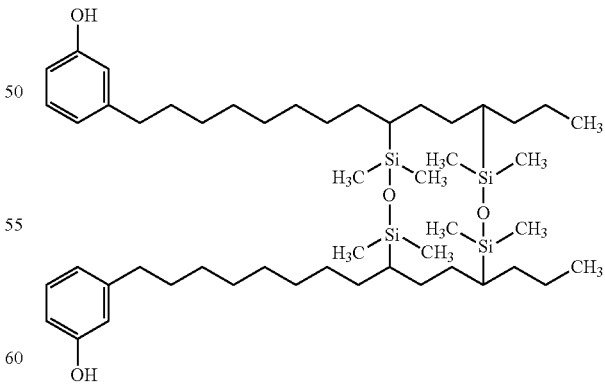

The cardanol dimers of the present invention have numerous uses. For example, the cardanol dimers may be used as a substitute for bis-phenyl molecules in applications where the cardanol dimers provide desirable properties, or the cardanol dimers may be used to form friction particles. As described below, the cardanol dimers may also be used to prepare epoxies and curing agents used, for example, in coatings.

In a preferred embodiment of the invention, z is 1, and there is no substitution at the $C_9$ location on the aliphatic side chain on the cardanol. The resulting dimer has the following structure:

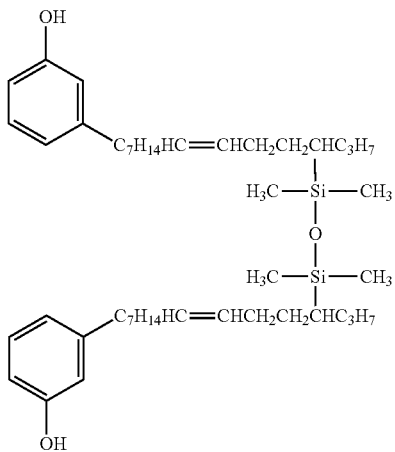

The resulting cardanol dimers of this embodiment may be further modified as described in detail below to include additional silane or fluorosilane groups bound to the aliphatic side chains on the cardanol dimers. These cardanol dimers may be used, for example, as raw materials to produce epoxies and curing agents used in epoxy coatings, such as coatings having improved anti-fouling properties for use in marine vessels.

In another embodiment of the invention, a long chain silicone cardanol dimer is formed by joining two cardanol molecules by a silicone based polymer. In one embodiment, the silicone based polymer is a polydimethylsiloxane of the formula:

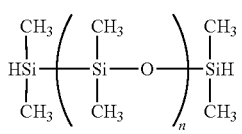

Where n=5-200. The resulting cardanol dimers are shown in FIG. 14. These cardanol dimers may be used to form epoxy resins or curing agents as described in detail below.

The following descriptions of preferred processes for producing the cardanol dimers and products formulated using the cardanol dimers are intended as examples only and are not intended to limit the full scope of the invention described and claimed.

Figure 2A:
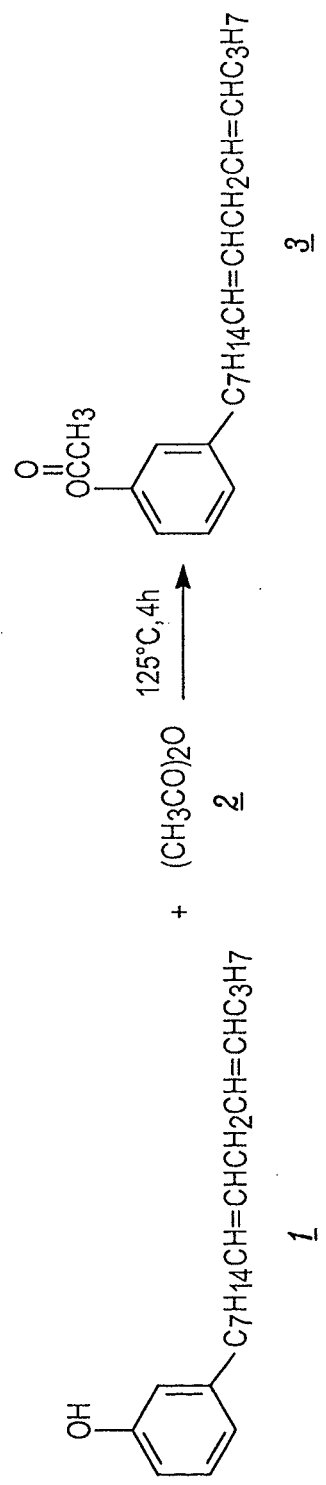
FIGS. 2A and 2B are schematics showing a process for synthesis of a cardanol silane dimer from cardanol.
Figure 2B:
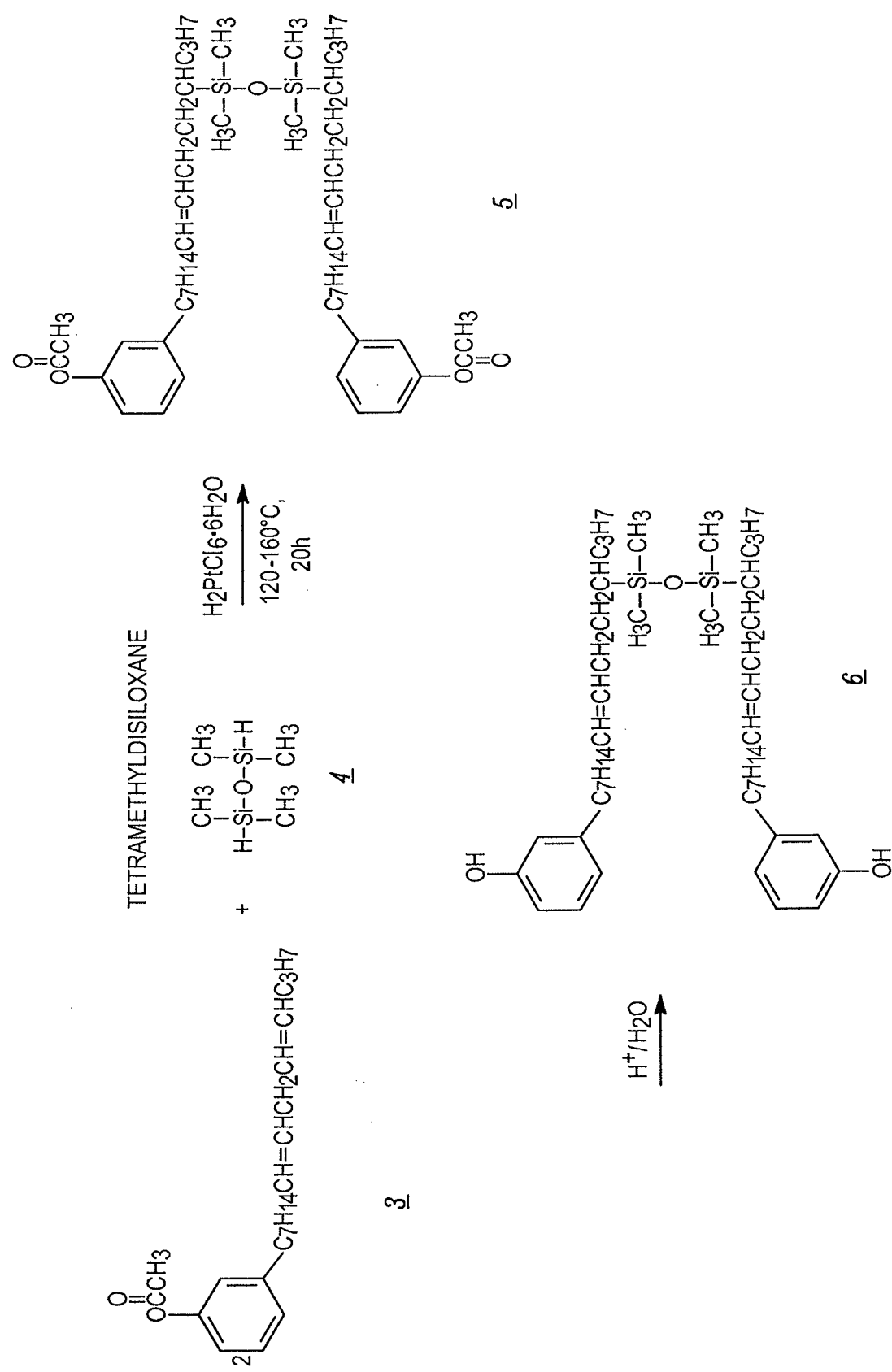

As shown in FIGS. 2A and 2B, in one embodiment of the invention, cardanol (1) is combined with acetic anhydride ($(CH_3CO)_2O$) (2), in an appropriate reactor and mixed at a temperature of between about 120° C. to 125° C. for between about 3 and 4 hours. In a preferred embodiment, the cardanol (1) and the acetic anhydride (2) are mixed at a temperature of about 125° C. for a period of about 4 hours. The reactor is preferably equipped with a mechanical agitation device to mix the reactants and a temperature control mechanism, such as a thermocouple device, to control the temperature in the reactor. An excess of acetic anhydride is provided to obtain maximum reaction of the cardanol. In one embodiment, the mole ratio of cardanol to acetic anhydride is 1:1.23. As shown in FIGS. 2A and 2B, the cardanol and acetic anhydride react and the hydroxyl group on the benzene ring of the cardanol molecule is replaced by an acetate group to form 3-(pentadecyl)-phenyl acetate, referred to herein as "acetate substituted cardanol" (3).

As further shown in FIGS. 2A and 2B, the acetate substituted cardanol (3) is combined with tetramethyldisiloxane (TMDS) (4) in an appropriate reactor in the presence of a catalyst to form an acetate substituted cardanol silane dimer (5). The reactor is preferably equipped with a mechanical agitation device to mix the reactants. A thermocouple temperature control mechanism may be used to control the temperature in the reactor. The acetate substituted cardanol is provided in excess of the stoichiometric amount to obtain maximum reaction with the TMDS. In one embodiment, the mole ratio of TMDS to acetate substituted cardanol is 1:6.

Any appropriate catalyst known to those skilled in the art may be used to catalyze the reaction. In particular, platinum containing catalysts that may be used in hydrolization reactions can be used to catalyze the reaction. For example, any of the following catalysts may be used: $H_2PtO_46H_2O$; $PtO_2$; $O[Si(CH_3)_2CH=CH_2]_2Pt$; $Pt[(VMe_2Si)_2O]$ [$ViMe_2SiOSiM$]. In a preferred embodiment, the catalyst is chloroplatinic acid ($H_2PtCl_66H_2O$). The reactor is maintained at a temperature of between about 120° C. to about 160° C. for a period of about 20 hours. As shown in FIG. 2, acetate substituted cardanol silane dimers (5) are formed by cross-linking acetate substituted cardanol molecules with the TMDS. The double bond between $C_{11}$ and $C_{12}$ on the pentadeca-8,11-diene portion of two cardanol molecules are reduced and Si—C bonds are formed between the pentadeca-8,11-diene and the TMDS. The acetate substituted cardanol silane dimer thus formed is then hydrolized with acid to remove the acetate group on the benzene ring of the cardanol and substitute a hydroxyl group to form a cardanol silane dimer (6). The hydrolization step can be performed using, for example, sulfuric acid or, preferably, hydrochloric acid. The acid wash step is preferably performed at a temperature of about 80° C. and at a pH of about 0.6.

The cardanol silane dimer formed by the process described above has a viscosity at 25° C. of approximately 150 cP, an iodine number of 125, and a dimer % by weight of about 95.3. As described below, the resulting cardanol silane dimers may be further processed to bond further silane groups to the cardanol silane dimer.

Figure 3:
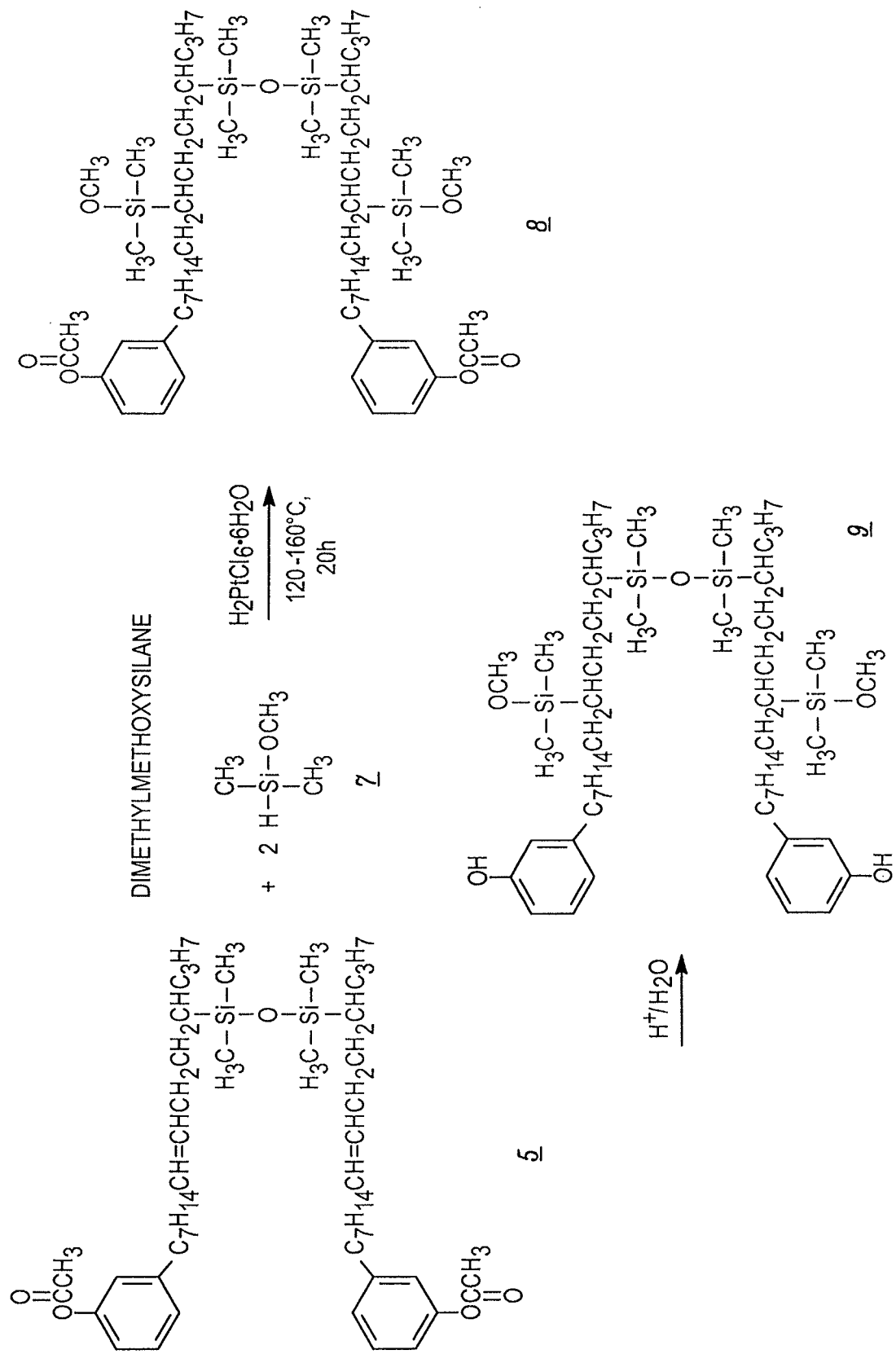
FIG. 3 is a schematic showing a process for synthesis of a cardanol silane dimer having an enhanced silane content.

As shown in FIG. 3, the acetate substituted cardanol silane dimer (5) fowled by the process described above may be combined with dimethylmethoxysilane (7) in a reactor in the presence of a catalyst. In particular, platinum containing catalysts that may be used in hydrosilyation reactions can be used to catalyze the reaction. For example, any of the following catalysts may be used: $H_2PtO_46H_2O$; $PtO_2$; $O[Si(CH_3)_2CH=CH_2]_2Pt$; $Pt[(VMe_2Si)_2O][ViMe_2SiOSiM]$. In a preferred embodiment, the catalyst is chloroplatinic acid ($H_2PtCl_66H_2O$). After combining the reactants and the catalyst in the reactor, the temperature is maintained between about 120° C. and 160° C. for a period of about 20 hours. The reactor is preferably equipped with a mechanical agitation device to mix the reactants and a temperature control mechanism, such as a thermocouple device, to control the temperature in the reactor. An excess of dimethylmethoxysilane is provided to obtain maximum reaction with the cardanol silane dimers. In one embodiment, the mole ratio of cardanol silane dimer to dimethylmethoxysilane is 1:4.

The acetate substituted cardanol silane dimer and the dimethylmethoxysilane react to form an acetate substituted cardanol silane dimer having additional silane groups at the $C_9$ location on the pentadeca-8,11-diene portion of the cardanol (8). The resulting acetate substituted cardanol silane dimer is then hydrolyzed with acid to remove the acetate group from the benzene ring and substitute a hydroxyl group to form a cardanol silane dimer having additional silane groups (9). The hydrolyzation step can be performed using, for example, sulfuric acid or, preferably, hydrochloric acid. The hydrolyzation step is preferably performed at a temperature of about 80° C. and at a pH of about 0.6.

Figure 4:
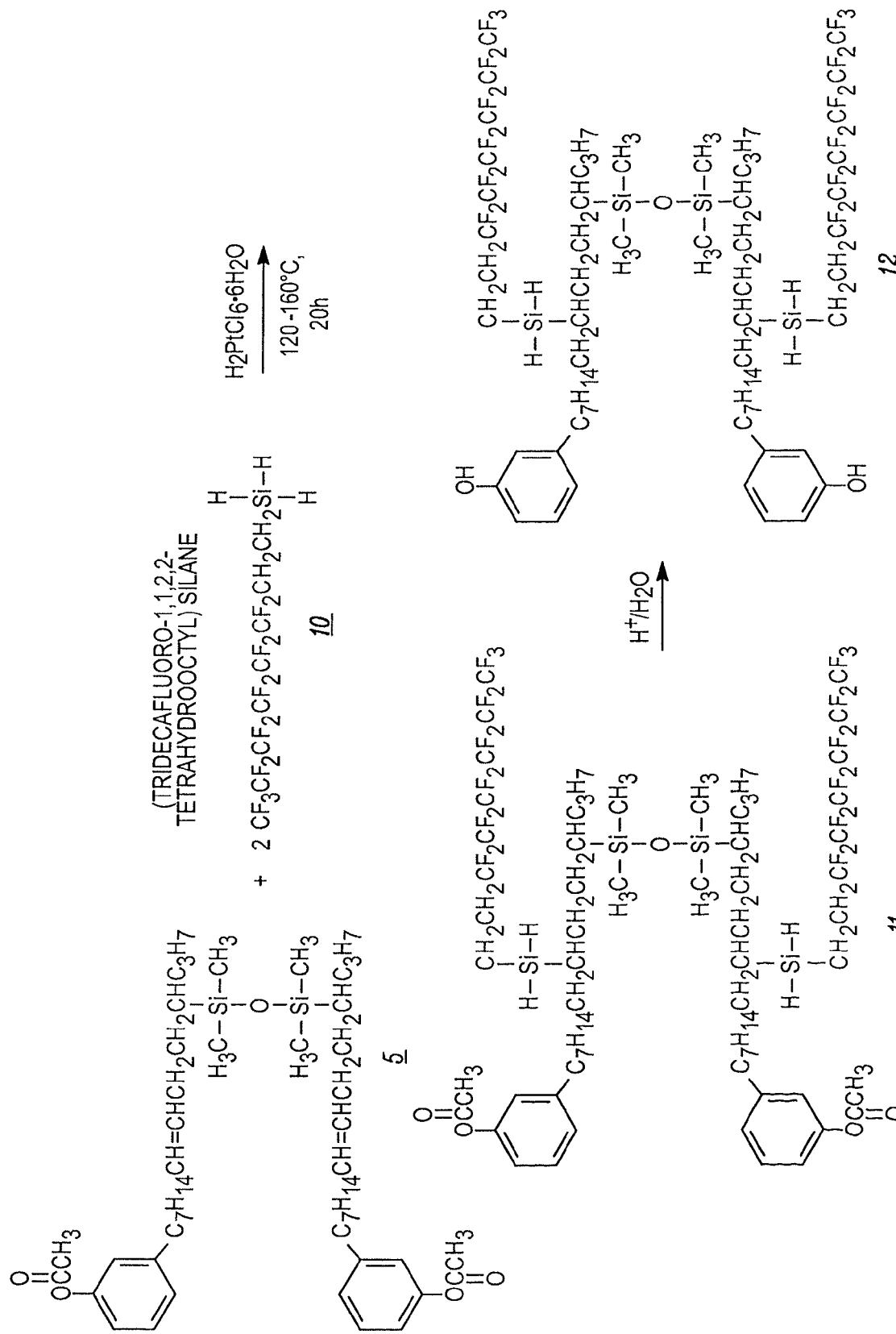
FIG. 4 is a schematic showing a process for synthesis of a cardanol silane dimer having a fluorinated silane.

In another embodiment of the present invention, fluoronated silane groups may be substituted on the cardanol silane dimer. As shown in FIG. 4, the acetate substituted cardanol silane dimer (5) formed by the process described above may be combined with (tridecafluoro-1,1,2,2 tetrahydrooctyl)silane (10) in the presence of a catalyst. In particular, platinum containing catalysts that may be used in hydrolization reactions can be used to catalyze the reaction. For example, any of the following catalysts may be used: $H_2PtO_4 6H_2O$; $PtO_2$; $O[Si(CH_3)_2CH=CH_2]_2Pt$; $Pt[(VMe_2Si)_2O][ViMe_2SiOSiM]$. In a preferred embodiment, the catalyst is chloroplatinic acid ($H_2PtCl_6 6H_2O$). After combining the reactants and the catalyst in the reactor, the temperature is maintained between about 120° C. and 160° C. for a period of about 20 hours. The reactor is preferably equipped with a mechanical agitation device to mix the reactants and a temperature control mechanism, such as a thermocouple device, to control the temperature in the reactor. An excess of (tridecafluoro-1,1,2,2 tetrahydrooctyl)silane is provided to obtain maximum reaction with the cardanol silane dimers. In one embodiment, the mole ratio of cardanol silane dimer to (tridecafluoro-1,1,2,2 tetrahydrooctyl)silane is 1:4.

The acetate substituted cardanol silane dimer (5) and the (tridecafluoro-1,1,2,2 tetrahydrooctyl)silane (10) react to form an acetate substituted cardanol silane dimer having (tridecafluoro-1,1,2,2 tetrahydrooctyl)silane groups at the $C_9$ location on the meta-substituted aliphatic carbon portion of the cardanol (11). The resulting acetate substituted cardanol silane dimer is then hydrolyzed with acid to remove the acetate group from the benzene ring and substitute a hydroxyl group to form a cardanol silane dimer having (tridecafluoro-1,1,2,2 tetrahydrooctyl)silane groups (12). The hydrolyzation step can be performed using, for example, sulfuric acid or, preferably, hydrochloric acid. The hydrolization step is preferably performed at a temperature of about 80° C. and at a pH of about 0.6.

One of the uses of the cardanol silane dimers described above is in curing agents and epoxy components that may be used in anti-fouling coatings for ships hulls or marine structures. The cardanol silane dimers prevent foulants form adhering to the hull or marine structure and thereby prevent fouling of the structure.

Figure 5:
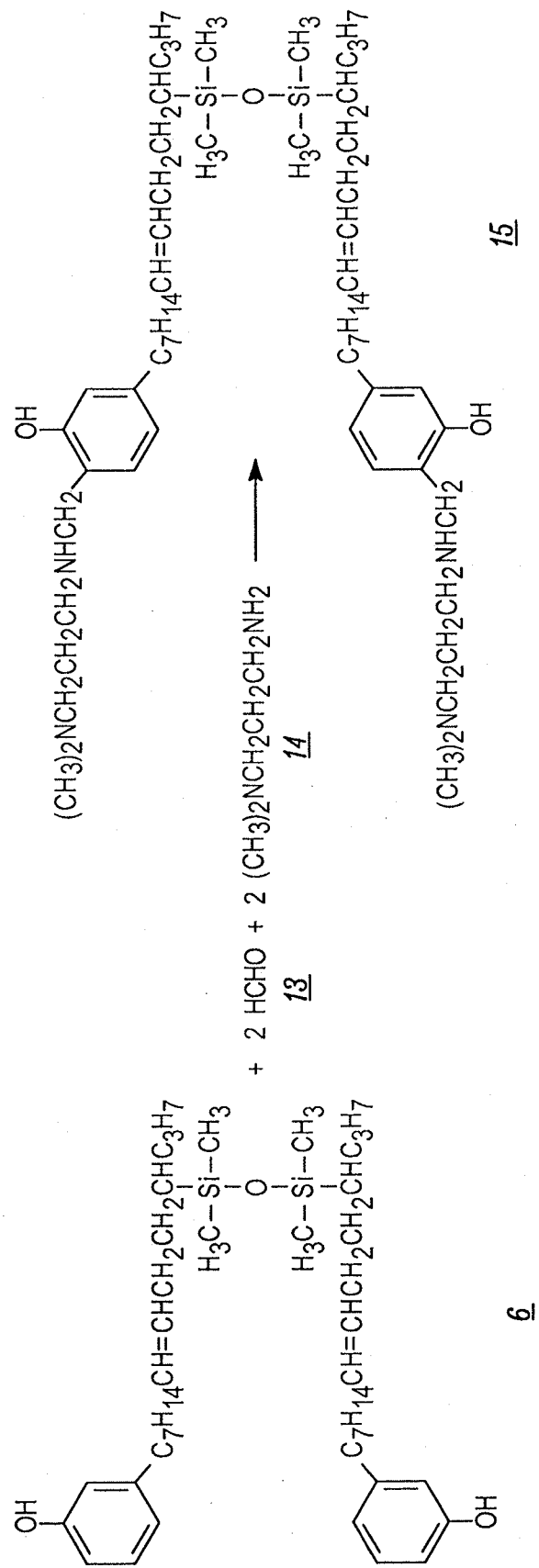
FIG. 5 is a schematic showing a process for synthesis of a curing agent for the anti-fouling coating from the cardanol silane dimer.

As shown in FIG. 5, in one embodiment, a curing agent for an epoxy may be synthesized by combining the cardanol silane dimer (6) produced as described above with paraformaldehyde (13) and an amine in a Mannich reaction. In the shown in FIG. 5, the amine is dimethylaminopropylamine (14). The reactants may be combined in any appropriate reactor with agitation and a temperature control mechanism, such as, for example, a thermocouple device. The reactants are mixed at a temperature of between about 70° C. to about 80° C. for a period of about 4 to about 6 hours. The paraformaldehyde and the dimethylaminopropylamine are provided in excess relative to the cardanol silane dimer. In one embodiment the mole ratio of dimer to paraformaldehyde to dimethylaminopropylamine is 1:2.4:2.4.

The paraformaldehyde (13) and dimethylaminopropylamine (14) react with the cardanol silane dimer (6) to form a dimethylaminopropylaminomethyl cardanol silane dimer curing agent (15). The resulting curing agent has a viscosity at 25° C. of about 70,300 cP, an amine value of 186 and a gel time of 48.7.

Figure 6:
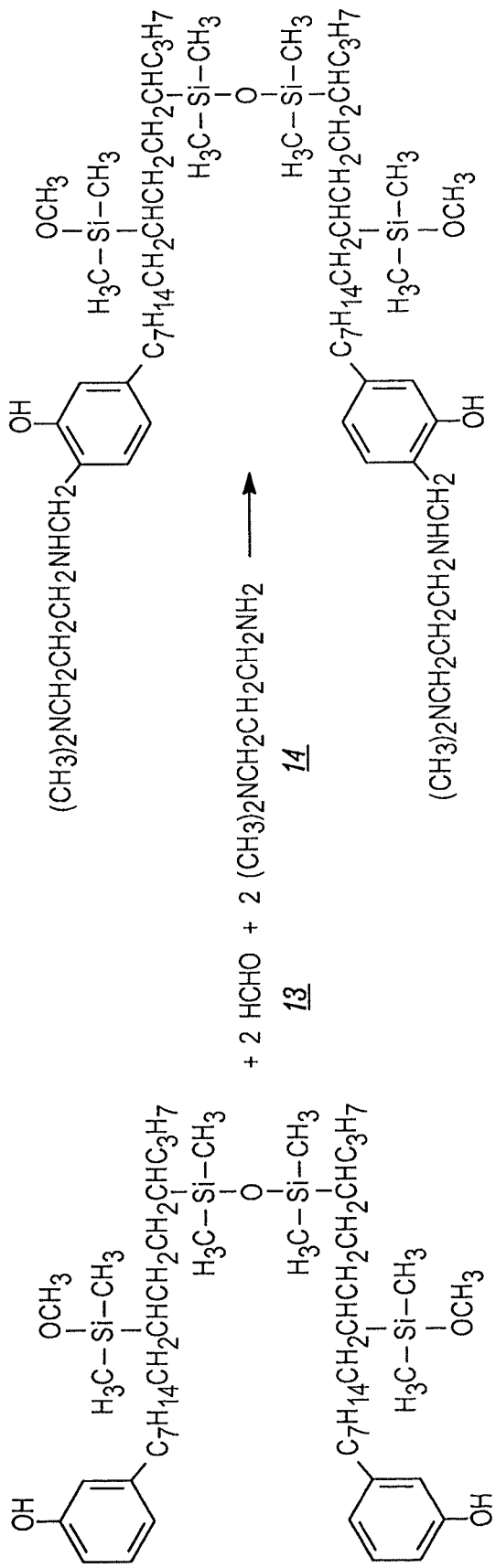
FIG. 6 is a schematic showing a process for synthesis of a curing agent for the anti-fouling coating from the cardanol silane dimer having an enhanced silane content.

As shown in FIG. 6, in another embodiment, the curing agent component may be synthesized by combining the silane substituted cardanol silane dimer (9) produced as described above with paraformaldehyde (13) and an amine in a Mannich reaction. In the embodiment shown in FIG. 6, the amine is dimethylaminopropylamine (14). The reactants may be combined in any appropriate reactor with agitation and a temperature control mechanism, such as, for example, a thermocouple device. The reactants are mixed at a temperature of between about 70° C. to about 80° C. for a period of about 4 to about 6 hours. The paraformaldehyde and the dimethylaminopropylamine are provided in excess relative to the silane substituted cardanol silane dimer. In one embodiment the mole ratio of dimer to paraformaldehyde to dimethylaminopropylamine is 1:2.4:2.4. The paraformaldehyde (13) and dimethylaminopropylamine (14) react with the silane substituted cardanol silane dimer (6) to form a dimethylaminopropylaminomethyl silane substituted cardanol silane dimer curing agent (16).

Figure 7:
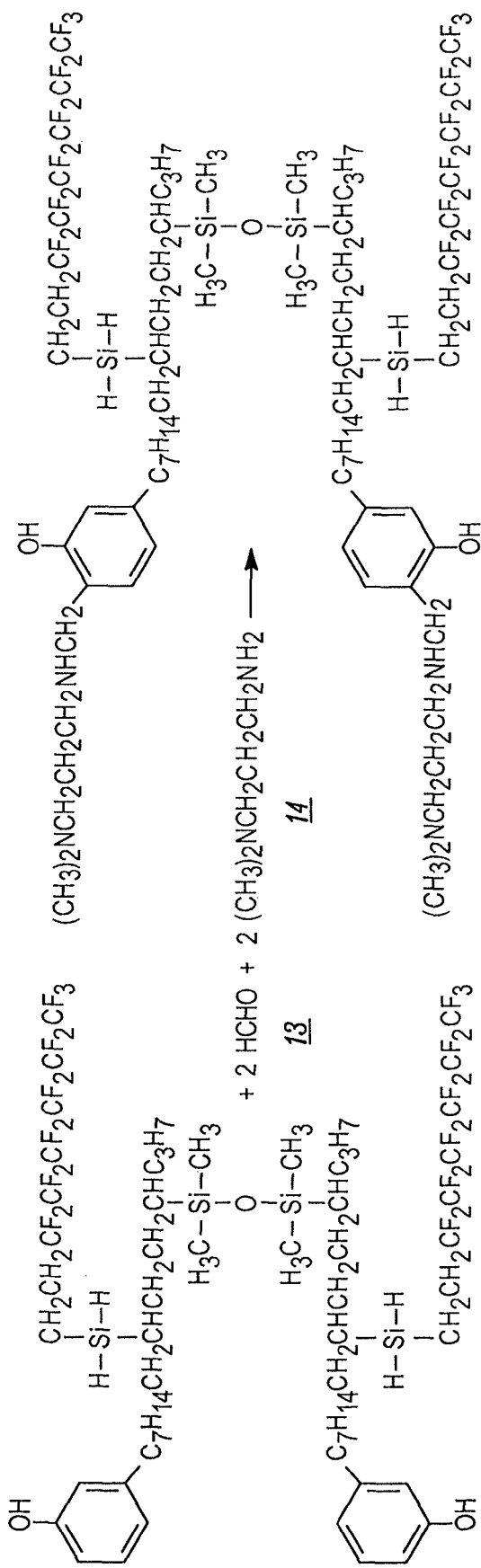
FIG. 7 is a schematic showing a process for synthesis of a curing agent for the anti-fouling coating from the cardanol silane dimer having a fluorinated silane.

As shown in FIG. 7, in yet another embodiment, the curing agent component may be synthesized by combining the fluorosilane cardanol silane dimer (12) produced as described above with paraformaldehyde (13) and an amine in a Mannich reaction. In the embodiment shown in FIG. 7, the amine is dimethylaminopropylamine (14). The reactants may be combined in any appropriate reactor with agitation and a temperature control mechanism, such as, for example, a thermocouple device. The reactants are mixed at a temperature of between about 70° C. to about 80° C. for a period of about 4 to about 6 hours. The paraformaldehyde and the dimethylaminopropylamine are provided in excess relative to the fluorosilane substituted cardanol silane dimer. In one embodiment the mole ratio of dimer to paraformaldehyde to dimethylaminopropylamine is 1:2.4:2.4. The paraformaldehyde (13) and dimethylaminopropylamine (14) react with the fluorosilane cardanol silane dimer (12) to form a fluorosilane dimethylaminopropylaminomethyl cardanol silane dimer curing agent (17).

Figure 8:
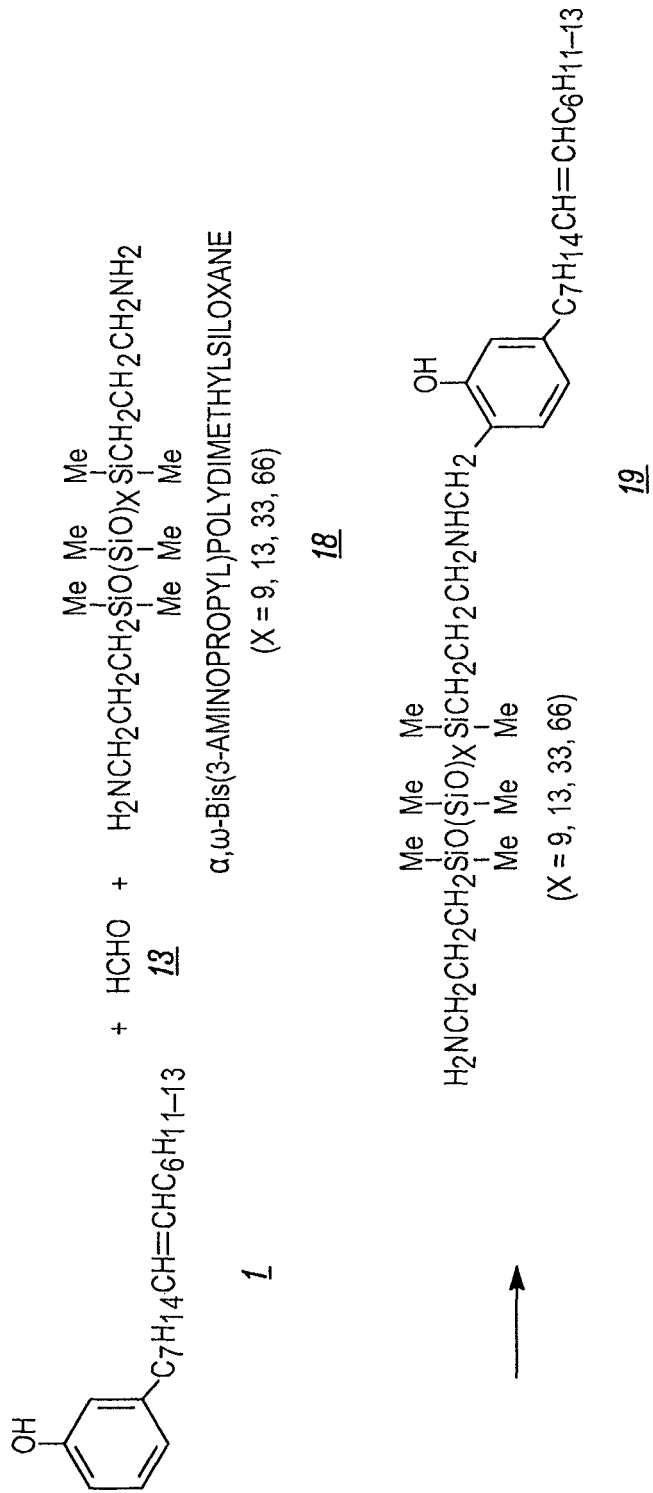
FIG. 8 is a schematic showing a process for synthesis of a curing agent from cardanol and an aminopropylsiloxane.

In another embodiment, the curing agent is synthesized from cardanol and 1,3-Bis (3-aminopropyl) polydimethylsiloxane. As shown in FIG. 8, cardanol (1), paraformaldehyde (13) and 1,3-Bis(3-aminopropyl)polydimethylsiloxane (18) are combined in an appropriate reactor with agitation and a temperature control mechanism, such as, for example, a thermocouple device. The reactants are mixed at a temperature of between about 70° C. to about 80° C. for a period of about 4 to about 6 hours. The paraformaldehyde and the 1,3-Bis(3-aminopropyl)polydimethylsiloxane are provided in excess relative to the cardanol. In a preferred embodiment the mole ratio of cardanol to paraformaldehyde to dimethylaminopropylamine is 1:1.2:1.2. In preferred embodiments, the 1,3-Bis (3-aminopropyl)polydimethylsiloxane has 9, 13, 33 or 66 dimethylsiloxane units. The 1,3-Bis(3-aminopropyl)polydimethylsiloxane bonds to the cardanol at the $C_5$ position on the phenol portion of the cardanol to form the 1,3-Bis(3-aminopropyl)polydimethylsiloxane modified cardanol (19) curing agent.

Figure 9A:
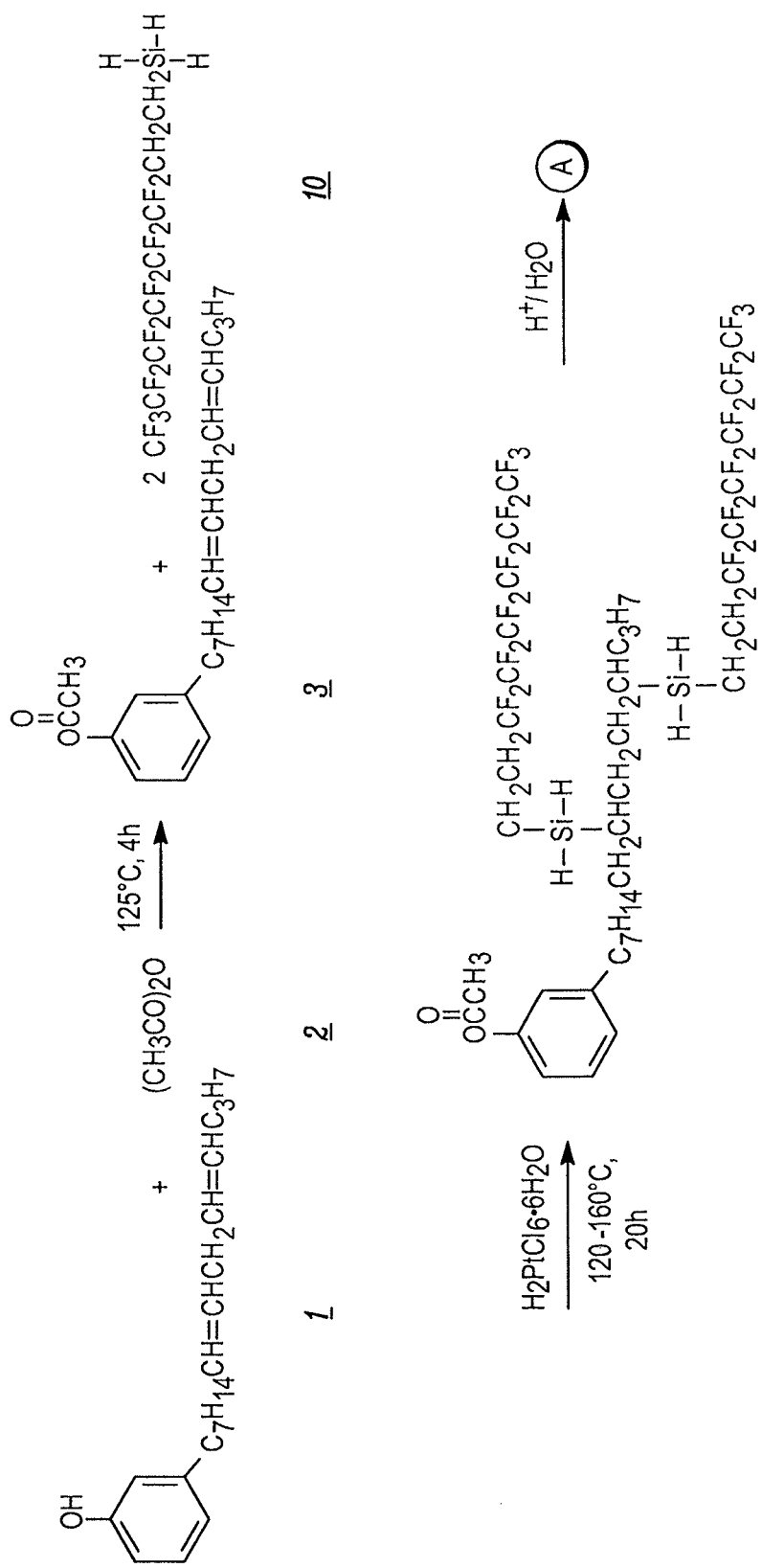
FIGS. 9A and 9B are schematics showing a process for synthesis of a curing agent from a cardanol having a fluorinated silane and an aminopropylsiloxane.
Figure 9B:
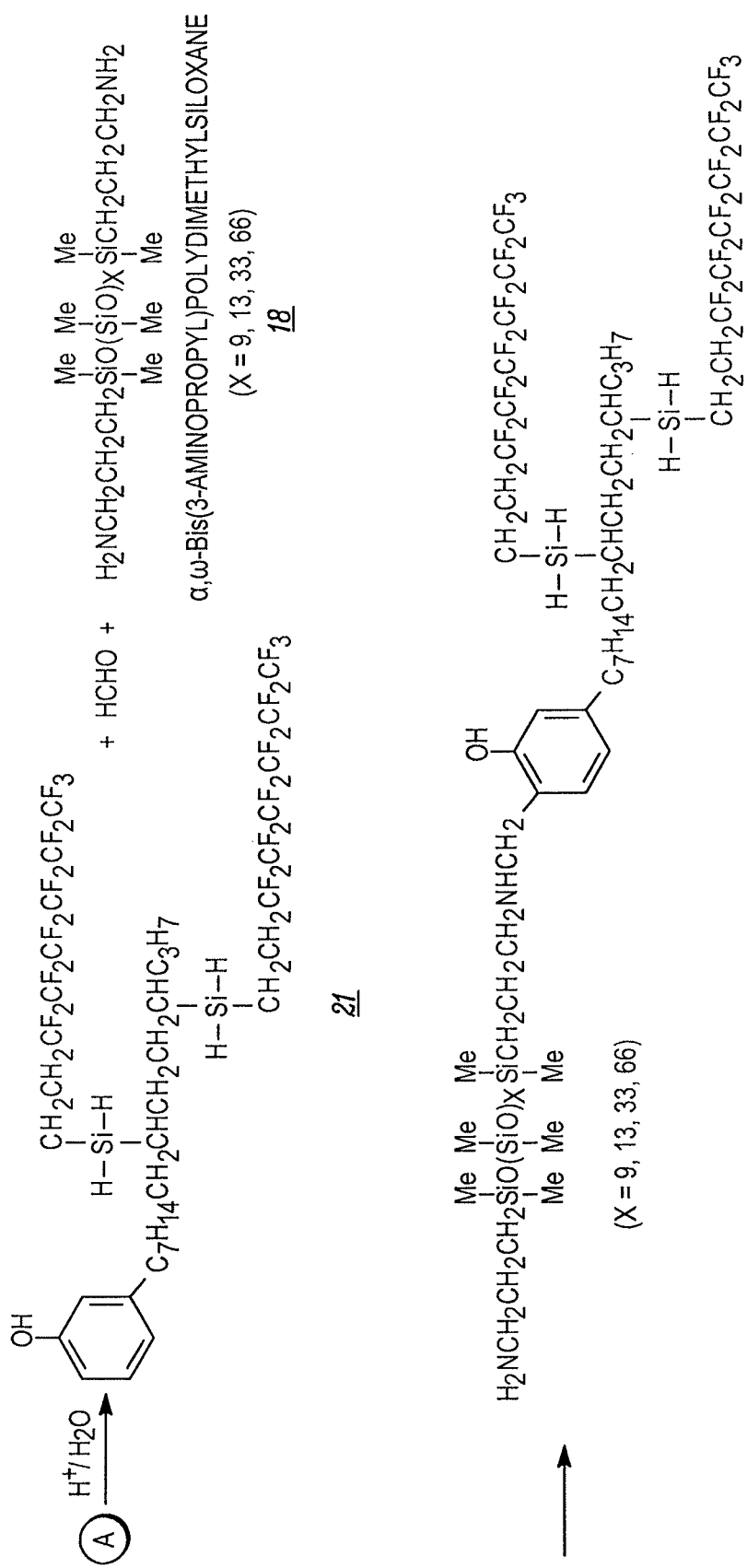

In another embodiment, a fluorosilane modified cardanol based curing agent is synthesized as shown in FIGS. 9A and 9B. Cardanol (1) and acetic anhydride (2) are combined in an appropriate reactor and maintained at a temperature of about 125° C. for about four hours as described above to produce an acetate substituted cardanol (3). The acetate substituted cardanol (3) is combined in an appropriate reactor with (tridecafluoro-1,1,2,2 tetrahydrooctyl)silane (10) in the presence of a catalyst. In particular, platinum containing catalysts that may be used in hydrolization reactions can be used to catalyze the reaction. For example, any of the following catalysts may be used: $H_2PtO_46H_2O$; $PtO_2$; $O[Si(CH_3)_2CH=CH_2]_2Pt$; $Pt[(VMe_2Si)_2O][ViMe_2SiOSiM]$. In a preferred embodiment, the catalyst is chloroplatinic acid ($H_2PtCl_66H_2O$). The acetate substituted cardanol and the (tridecafluoro-1,1,2,2 tetrahydrooctyl)silane are provided in stoichiometric molar amounts. After combining the reactants and the catalyst in the reactor, the temperature is maintained between about 120° C. and 160° C. for a period of about 20 hours. As shown in FIGS. 9A and 9B, the acetate substituted cardanol (3) and the (tridecafluoro-1,1,2,2 tetrahydrooctyl)silane (10) react to form an acetate substituted cardanol having (tridecafluoro-1,1,2,2 tetrahydrooctyl)silane groups at the $C_9$ and $C_{11}$ locations on the meta-substituted aliphatic carbon portion of the cardanol (20).

The resulting acetate substituted cardanol with the (tridecafluoro-1,1,2,2 tetrahydrooctyl)silane groups (20) is hydrolyzed with acid to remove the acetate group from the benzene ring and substitute a hydroxyl group to form cardanol with a (tridecafluoro-1,1,2,2 tetrahydrooctyl)silane group (21). The hydrolization step can be performed using, for example, sulfuric acid or, preferably, hydrochloric acid. The hydrolization step is preferably performed at a temperature of about 80° C. and at a pH of about 0.6.

As further shown in FIGS. 9A and 9B, the cardanol with a (tridecafluoro-1,1,2,2 tetrahydrooctyl)silane group (21), paraformaldehyde (13) and 1,3-Bis(3-aminopropyl)polydimethylsiloxane (18) are combined in a reactor and mixed at a temperature of between about 70° C. and about 80° C. for approximately 4 to 6 hours. In preferred embodiments, the 1,3-Bis(3-aminopropyl)polydimethylsiloxane has 9, 13, 33 or 66 dimethylsiloxane units. The 1,3-Bis(3-aminopropyl)polydimethylsiloxane bonds to the cardanol at the $C_9$ position on the phenol portion of the cardanol to form a 1,3-Bis(3-aminopropyl)polydimethylsiloxane modified cardanol with a (tridecafluoro-1,1,2,2 tetrahydrooctyl)silane group (22), which can be used as a curing agent.

Figure 10A:
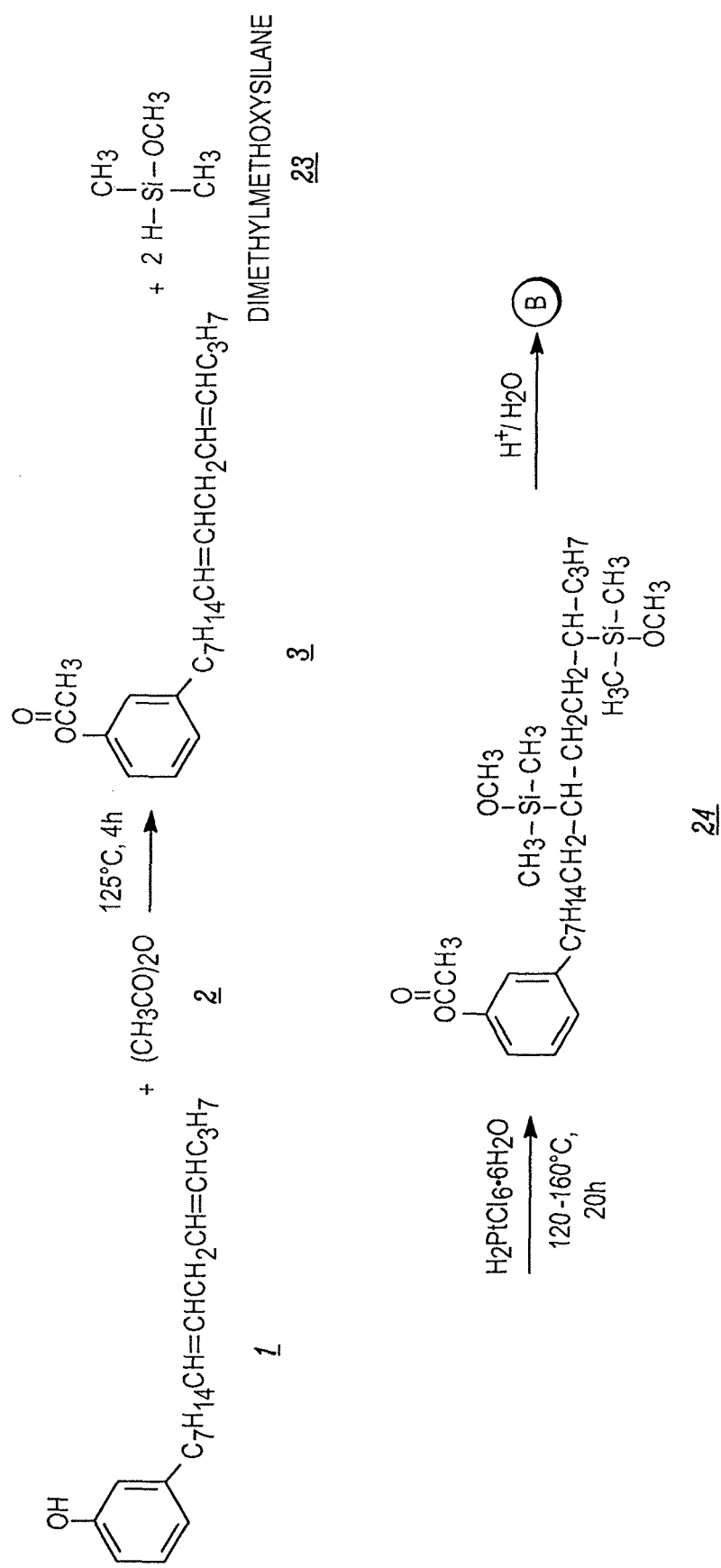
FIGS. 10A and 10B are schematics showing a process for synthesis of a curing agent from a cardanol having a silane group and an aminopropylsiloxane.
Figure 10B:
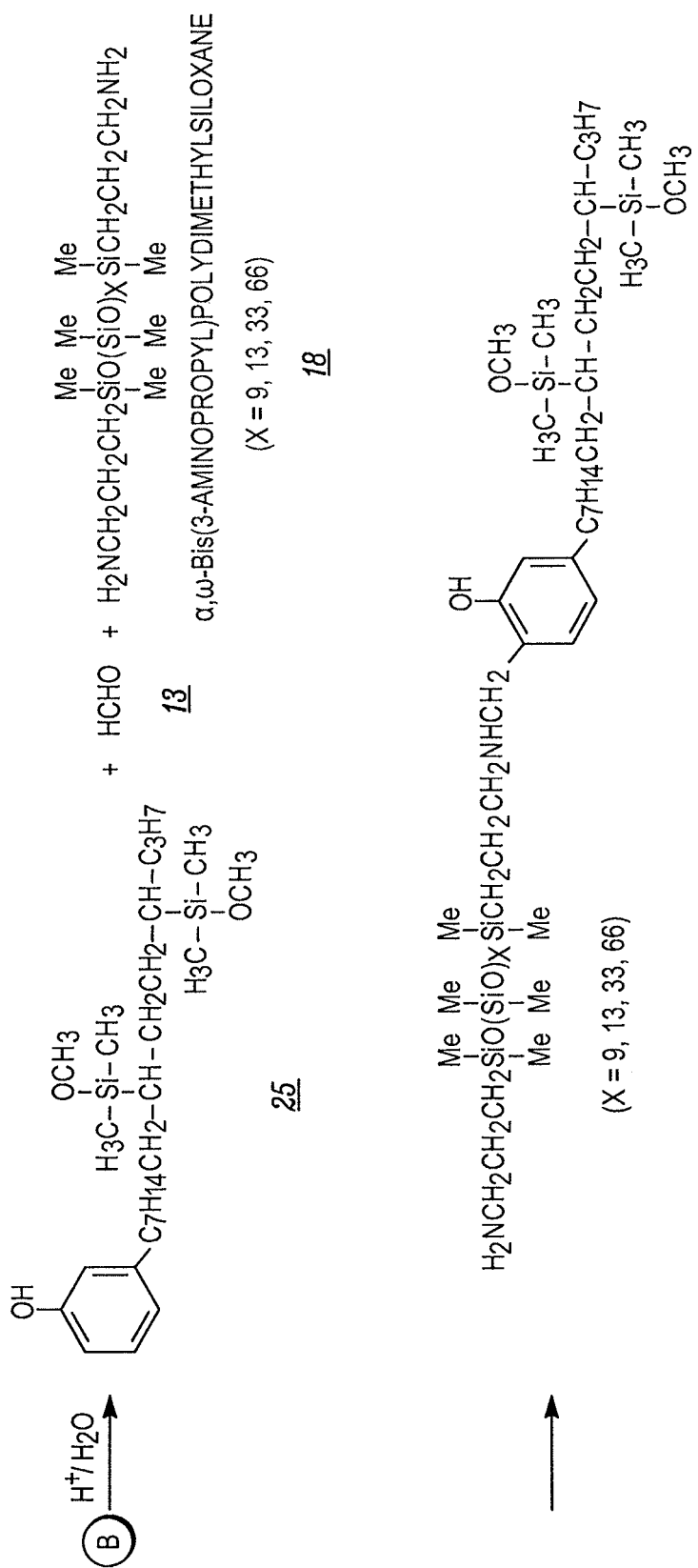

In yet another embodiment of the invention, a dimethylmethoxysilane modified cardanol based curing agent is synthesized as shown in FIGS. 10A and 10B. Cardanol (1) and acetic anhydride (2) are combined in a reactor and mixed at a temperature of about 125° C. for about four hours as described above to produce an acetate substituted cardanol (3). The acetate substituted cardanol (3) is combined with dimethylmethoxysilane (23) in the presence of a catalyst. In particular, platinum containing catalysts that may be used for hydrosilyation reactions can be used to catalyze the reaction. For example, any of the following catalysts may be used: $H_2PtO_46H_2O$; $PtO_2$; $O[Si(CH_3)_2CH=CH_2]_2Pt$; $Pt[(VMe_2Si)_2O][ViMe_2SiOSiM]$. In a preferred embodiment, the catalyst is chloroplatinic acid ($H_2PtCl_66H_2O$). After combining the reactants and the catalyst in the reactor, the temperature is maintained between about 120° C. and 160° C. for a period of about 20 hours. The dimethylmethoxysilane is provided in excess relative to the acetate substituted cardanol. In one embodiment, the mole ratio of acetate substituted cardanol to dimethylmethoxysilane is 1:3.

The acetate substituted cardanol (3) and the dimethylmethoxysilane (23) react to form an acetate substituted cardanol having a dimethylmethoxysilane group at the $C_9$ and $C_{11}$ locations on the meta-substituted aliphatic carbon portion of the cardanol (24). The resulting acetate substituted cardanol with the dimethylmethoxysilane groups (24) is hydrolyzed with acid to remove the acetate group from the benzene ring and substitute a hydroxyl group to form cardanol with substituted dimethylmethoxysilane groups (25). The hydrolization step can be performed using, for example, sulfuric acid or, preferably., hydrochloric acid. The hydrolization step is preferably performed at a temperature of about 80° C. and at a pH of about 0.6.

As further shown in FIGS. 10A and 10B, the cardanol with a dimethylmethoxvsilane group (25), paraformaldehyde (13) and 1,3-Bis(3-aminopropyl)polydimethylsiloxane (18) are combined in a reactor and mixed at a temperature of between 70° C. and 80° C. for approximately 4-6 hours. In preferred embodiments, the 1,3-Bis(3-aminopropyl)polydimethylsiloxane has 9, 13, 33 or 66 dimethylsiloxane units. The 1,3-Bis(3-aminopropyl)polydimethylsiloxane bonds to the cardanol at the $C_9$ position on the phenol portion of the cardanol to form a 1,3-Bis(3-aminopropyl)polydimethylsiloxane modified cardanol with a dimethylmethoxysilane group (26), which can be used as a curing agent.

Figure 11:
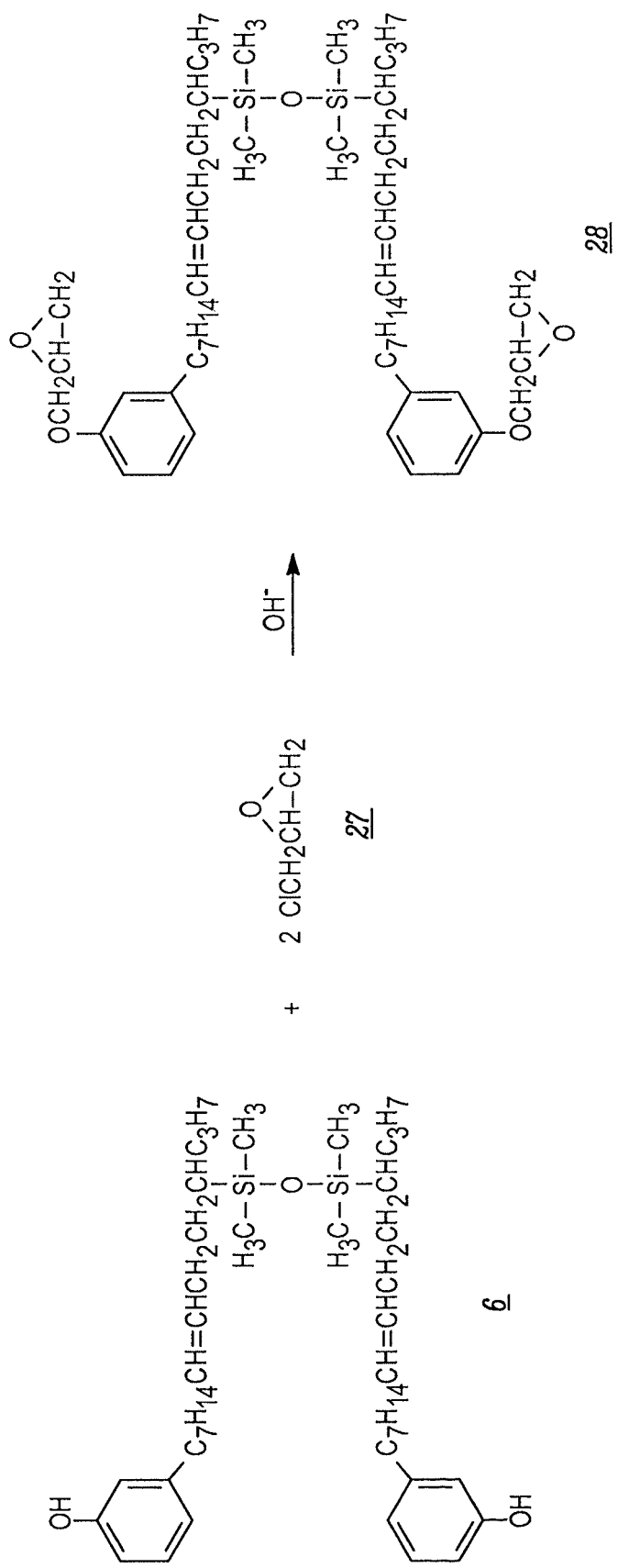
FIG. 11 is a schematic showing a process for synthesis of an epoxy resin from a cardanol silane dimer and epichlorohydrin.

The epoxy component of the anti-fouling coating is synthesized in an epoxidation reaction by combining any of the cardanol silane dimers described above with epichlorohydrin in a caustic soda solution, preferably a 50% caustic soda solution. As shown in FIG. 11, in one embodiment of the invention, the cardanol silane dimer (6) synthesized by the process described above and epichlorohydrin (27) are combined in a reactor with a 50% caustic soda solution. The epichlorohydrin is provided in excess relative to the cardanol silane dimer. In one embodiment, the mole ratio of cardanol silane dimer to epichlorohydrin is 1:6. The reactor is maintained at a temperature of between 65° C. and 70° C. for a period of approximately 3 to 4 hours. As shown in FIG. 11, the epichlorohydrin reacts with the hydroxyl groups on the benzene rings of the cardanol silane dimers to form the cardanol silane epoxy component (28) of the anti-fouling coating. The epoxy component has a viscosity at 25° C. of approximately 285 cPs, an EEW of 494, a volume loss of 2.7 and a hydrolysable Cl value of 3.6.

Figure 12:
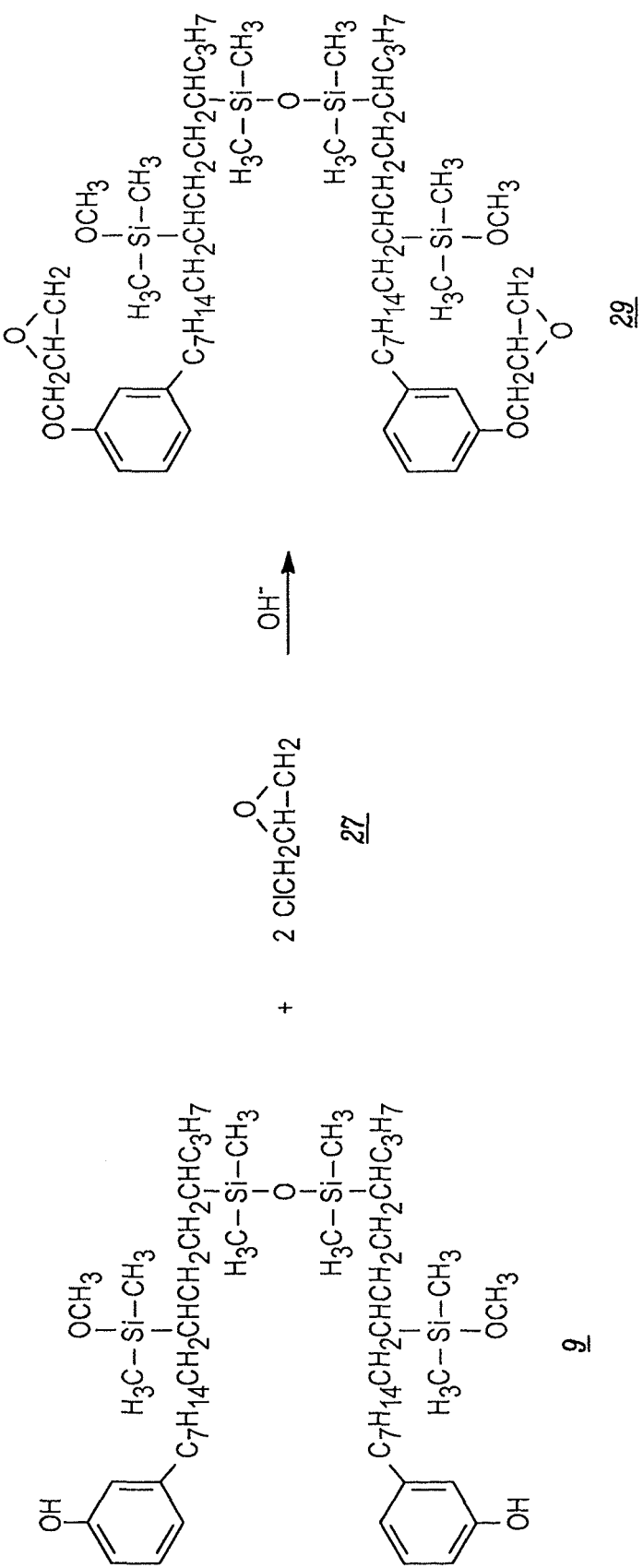
FIG. 12 is a schematic showing a process for synthesis of an epoxy resin from a cardanol silane dimer having an enhanced silane content and epicholorohydrin.

As shown in FIG. 12, in another embodiment of the invention, the silane substituted cardanol silane dimer (9) synthesized by the process described above is combined with epichlorohydrin (27) in a reactor with a caustic soda solution, preferably 50% caustic soda solution. The epichlorohydrin is provided in excess relative to the silane substituted cardanol silane dimer. In a preferred embodiment, the mole ratio of the silane substituted cardanol silane dimer to epichlorohydrin is 1:6. The reactor is maintained at a temperature of between 65° C. and 70° C. for a period of approximately 3-4 hours. As shown in FIG. 12, the epichlorohydrin reacts with the hydroxyl groups on the benzene rings of the cardanol silane dimers to form a silane substituted cardanol silane epoxy (29).

Figure 13:
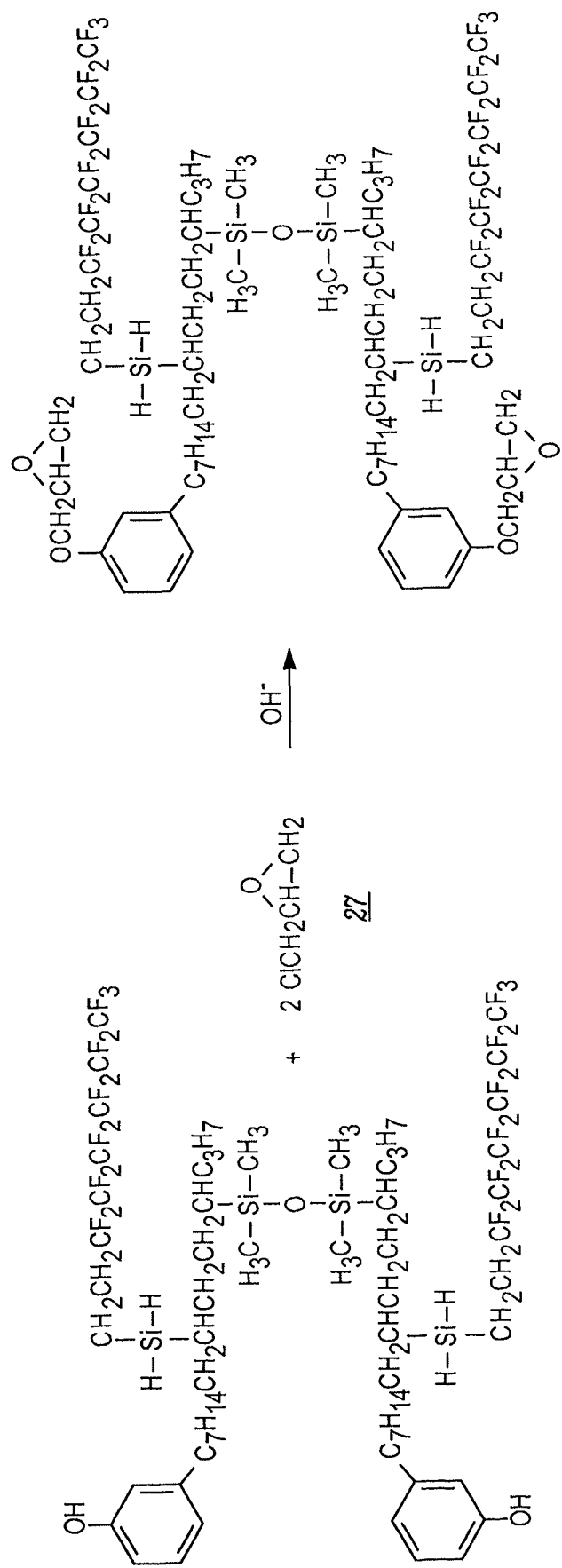
FIG. 13 is a schematic showing a process for synthesis of an epoxy resin from a cardanol silane dimer having a fluorinated silane and epichlorohydrin.

As shown in FIG. 13, in yet another embodiment of the invention, the cardanol silane dimer having substituted (tridecafluoro-1,1,2,2 tetrahydrooctyl)silane groups (12) synthesized by the process described above and epichlorohydrin (27) are combined in a reactor with a caustic soda solution, preferably a 50% caustic soda solution. The epichlorohydrin is provided in excess relative to the fluorosilane substituted cardanol silane dimer. In one embodiment, the mole ratio of fluorosilane substituted cardanol silane dimer to epichlorohydrin is 1:6. The reactor is maintained at a temperature of between 65° C. and 70° C. for a period of approximately 3 to 4 hours. As shown in FIG. 13, the epichlorohydrin reacts with the hydroxyl groups on the benzene rings of the cardanol silane dimer having (tridecafluoro-1,1,2,2 tetrahydrooctyl) silane groups to form a fluorosilane substituted cardanol silane epoxy (30).

Figure 14A:
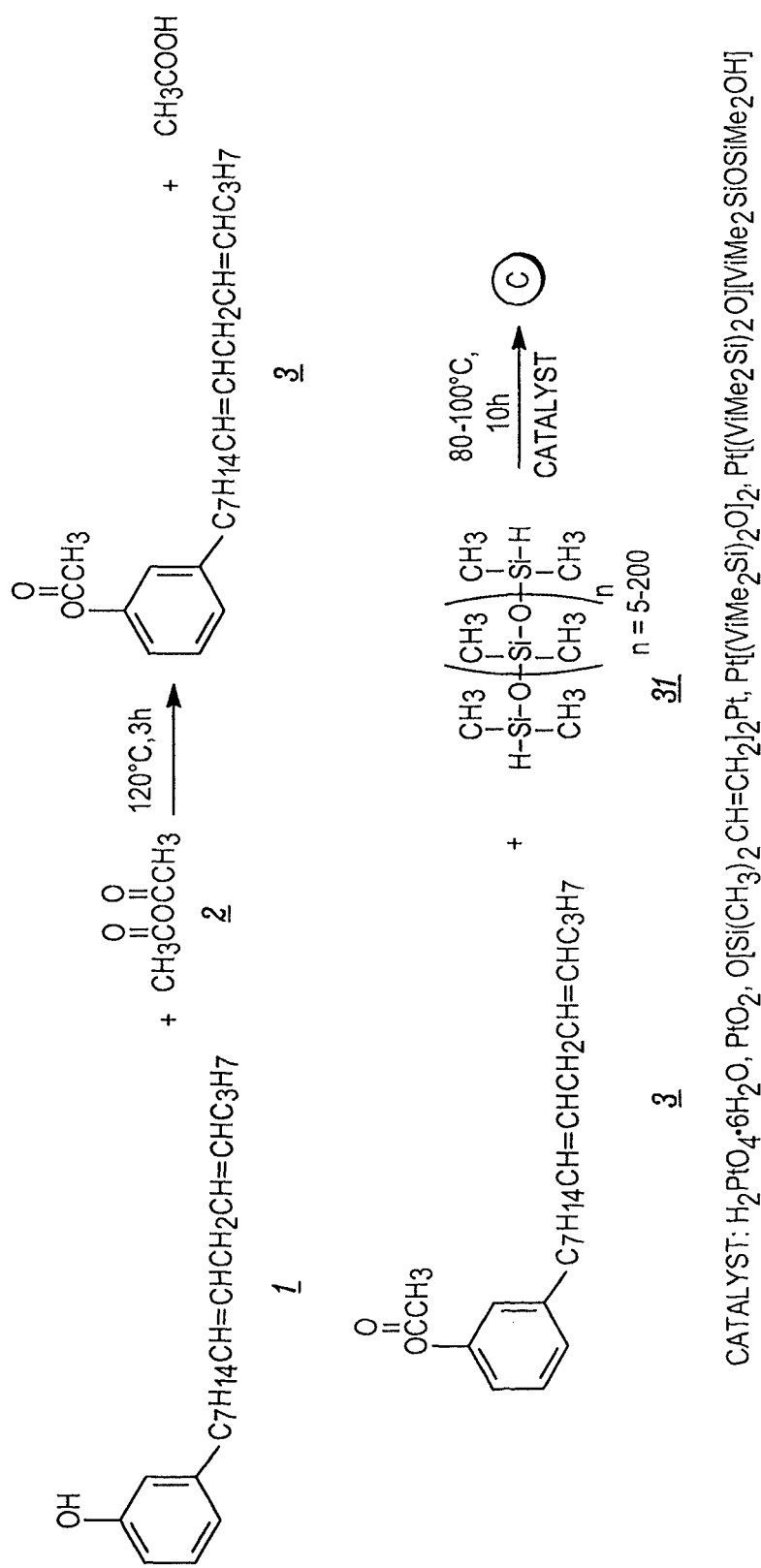
FIGS. 14A and 14B are schematics showing a process for the synthesis of a long chain silicone cardanol dimer.
Figure 14B:
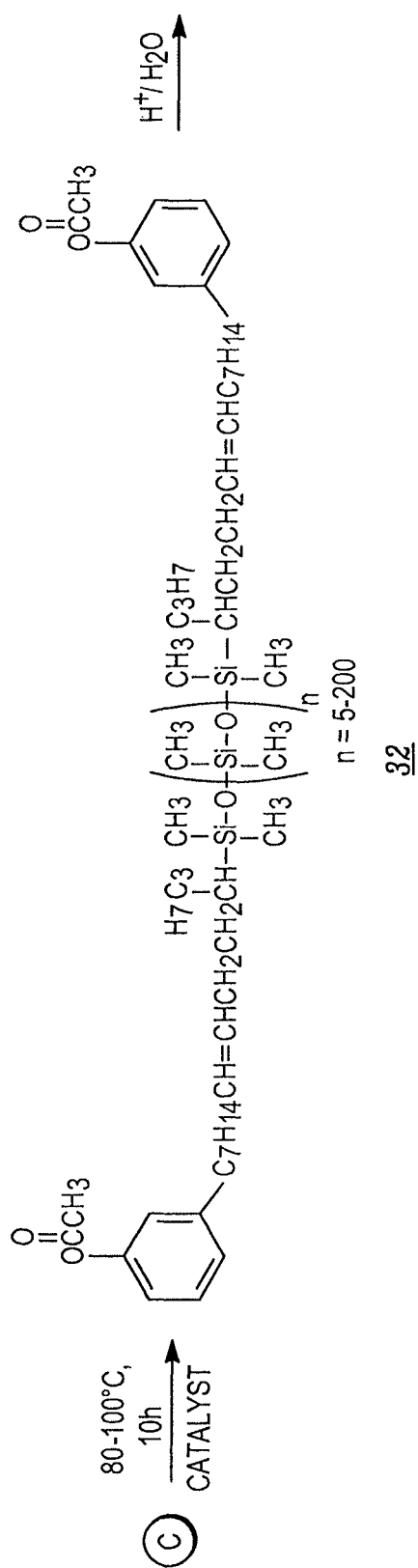
Figure 14B:
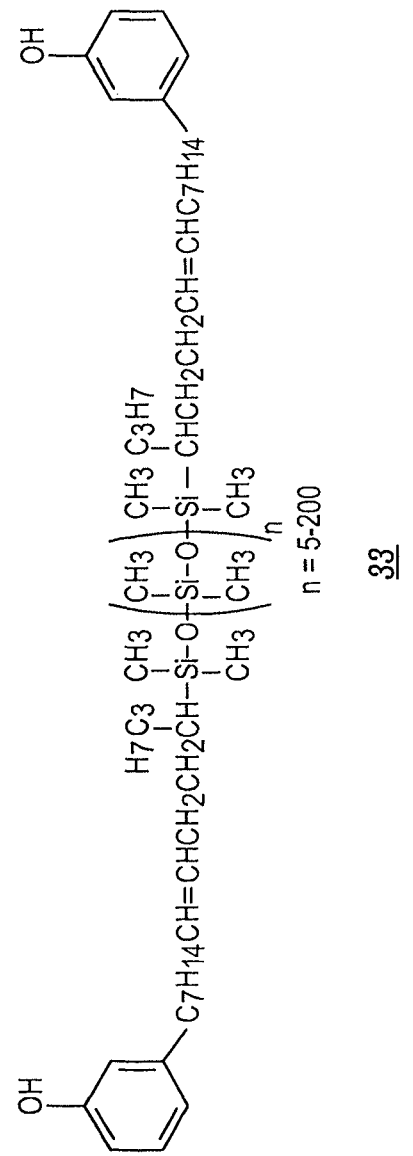

In another embodiment of the invention shown in FIGS. 14A and 14B, a long chain silicone cardanol dimer is formed. Cardanol (1) is combined with acetic anhydride (($CH_3CO)_2$ O) (2) in an appropriate reactor and maintained at a temperature of between about 120° C. to 125° C. for between about 3 and 4 hours. In a preferred embodiment, the cardanol (1) and the acetic anhydride (2) are mixed at a temperature of about 120° C. for a period of about 4 hours. The reactor is preferably equipped with a mechanical agitation device to mix the reactants and a temperature control mechanism, such as a thermocouple device, to control the temperature in the reactor. An excess of acetic anhydride is provided to obtain maximum reaction of the cardanol. In one embodiment, the mole ratio of cardanol to acetic anhydride is about 1:1.23. As shown in FIGS. 14A and 14B, the cardanol and acetic anhydride react and the hydroxyl group on the benzene ring of the cardanol molecule is replaced by an acetate group to form an acetate substituted cardanol (3).

As further shown in FIGS. 14A and 14B, the acetate substituted cardanol (3) is combined with a polydimethylsiloxane (31) in an appropriate reactor in the presence of a catalyst. The polydimethylsiloxane preferably has the following formula with n between 5 and 200.

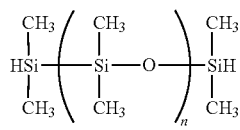

The reactor is preferably equipped with a mechanical agitation device to mix the reactants and a thermocouple temperature control mechanism to control the temperature in the reactor. The cardanol (3) and the polydimethylsiloxane (31) react to form an acetate substituted long chain silicone cardanol dimer. (32). The acetate substituted cardanol is provided in excess of the stoichiometric amount to obtain maximum reaction with the polydimethylsiloxane (31). In one embodiment, the mole ratio of polydimethylsiloxane to acetate substituted cardanol is 1:6.

Any appropriate catalyst known to those skilled in the art may be used to catalyze the reaction. In particular, platinum containing catalysts that may be used for hydrolization reactions can be used to catalyze the reaction. For example, any of the following catalysts may be used: $H_2PtO_46H_2O$; $PtO_2$; $O[Si(CH_3)_2CH=CH_2]_2Pt$; $Pt[(VMe_2Si)_2O]$ [$ViMe_2SiOSiM$]; or $H_2PtCl_66H_2O$. The reactor is maintained at a temperature of between about 80° C. to about 100° C. for a period of about 10 hours. As shown in FIGS. 14A and 14B, acetate substituted long chain silicone cardanol dimers (32) are formed by cross-linking acetate substituted cardanol molecules with the polydimethylsiloxane. The double bond between $C_{11}$ and $C_{12}$ on the pentadeca-8,11-diene portion of two cardanol molecules are reduced and Si—C bonds are formed between the pentadeca-8,11-diene and the polydimethylsiloxane. The acetate substituted long chain silicone cardanol dimer thus formed is then hydrolyzed with acid to remove the acetate group on the benzene ring of the cardanol and substitute a hydroxyl group to form a long chain silicone cardanol dimer (33). The hydrolization step can be performed using, for example, sulfuric acid or, preferably, hydrochloric acid. The hydrolization step is preferably performed at a temperature of about 80° C. and at a pH of about 0.6.

When n=5 on the polydimthylsiloxane, the long chain silicone cardanol dimer formed by the process described above has a viscosity at 25° C. of approximately 280 cP, and an iodine number of 102.

Figure 15:
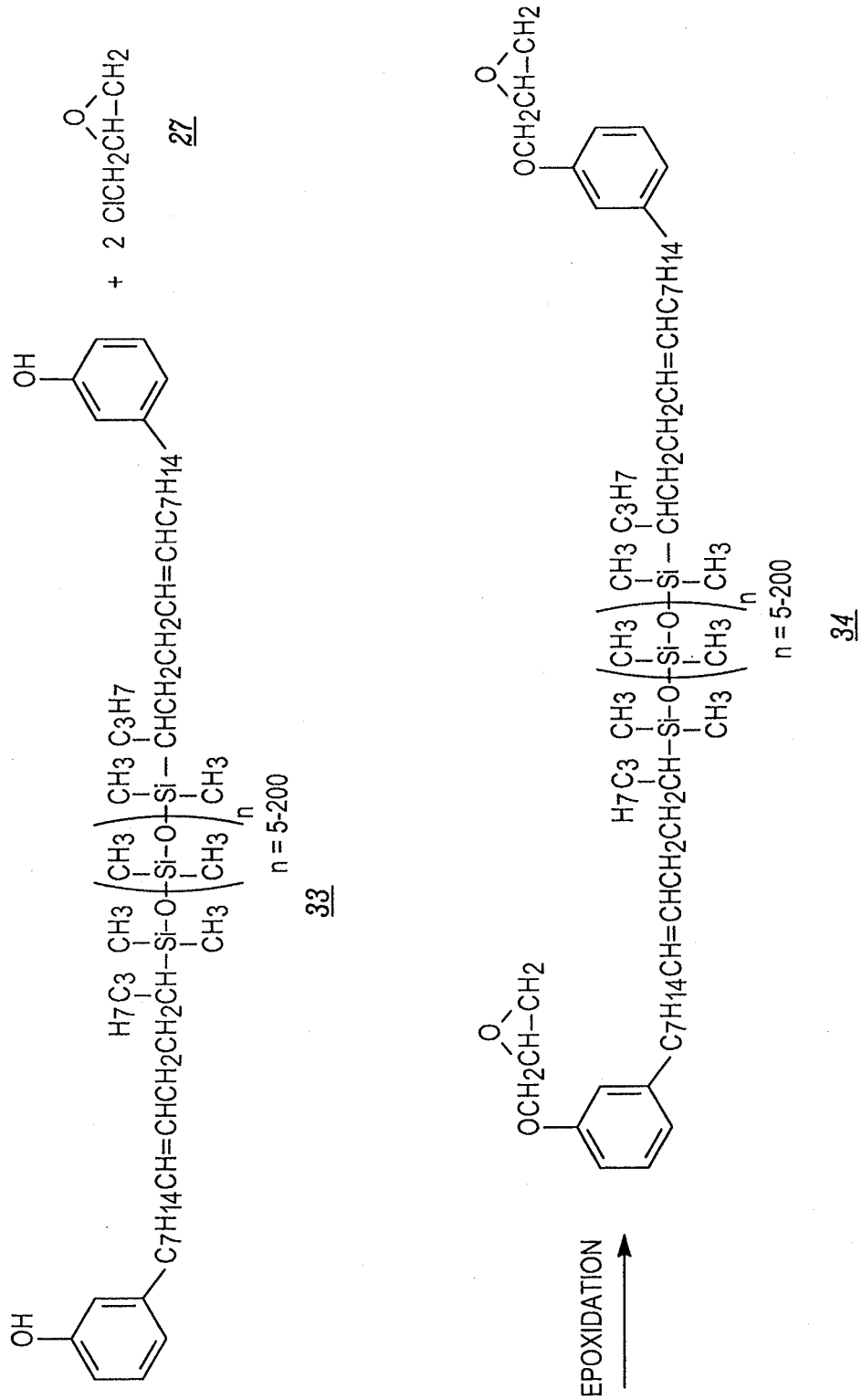
FIG. 15 is a schematic showing a process for the synthesis of an epoxy resin from a long chain silicone cardanol dimer.

The long chain silicone cardanol dimer may be used to produce an epoxy resin component and a curing agent for a coating that may be used as an anti-fouling coating. The epoxy resin component may be synthesized in an epoxidation reaction by combining the long chain silicone cardanol dimer described above with epichlorohydrin in a caustic soda solution, preferably a 50% caustic soda solution. As shown in FIG. 15, in one embodiment of the invention, the long chain silicone cardanol dimer (33) synthesized by the process described above and epichlorohydrin (27) are combined in a reactor with a 50% caustic soda solution. The epichlorohydrin is provided in excess relative to the long chain silicone cardanol dimer. In a preferred embodiment, the mole ratio of long chain silicone cardanol dimer to epichlorohydrin is 1:6. The reactor is maintained at a temperature of between 65° C. and 70° C. for a period of approximately 3 to 4 hours. As shown in FIG. 15, the epichlorohydrin reacts with the hydroxyl groups on the benzene rings of the long chain silicone cardanol dimers to form an epoxy component (34) which can be used in an anti-fouling coating.

Figure 16:
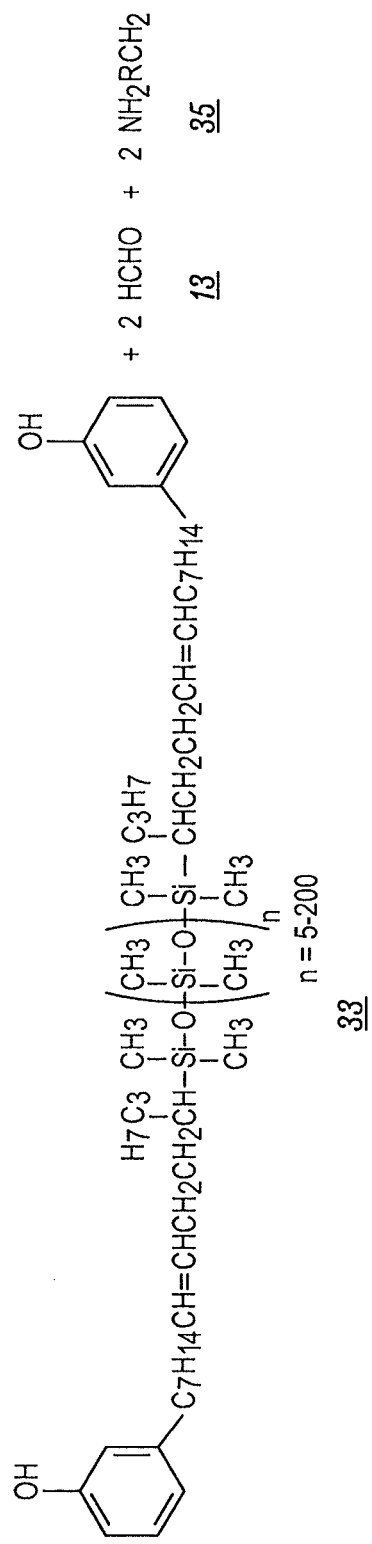
FIG. 16 is a schematic showing a process for the synthesis of a curing agent from a long chain silicone dimer.
Figure 16:
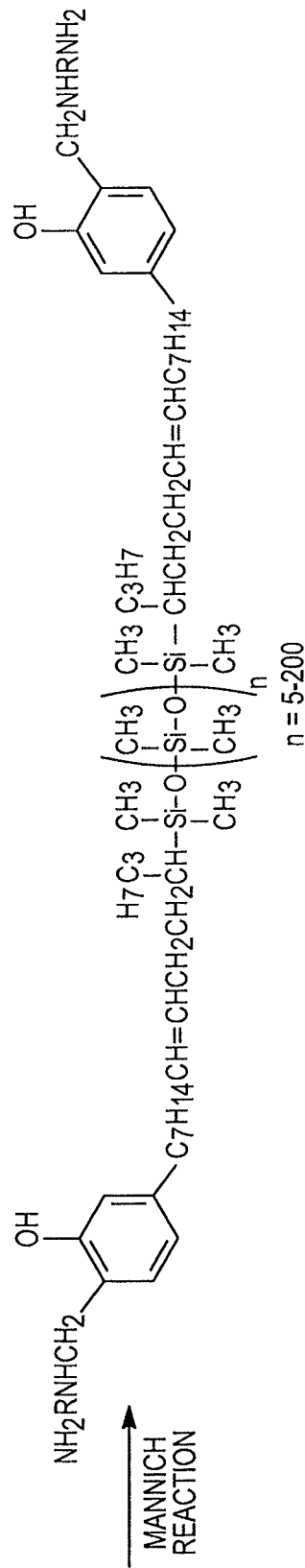

A curing agent for an epoxy may be synthesized by combining the long chain silicone cardanol dimer (33) produced as described above with paraformaldehyde (13) and an amine in a Mannich reaction. In one embodiment shown in FIG. 16, the amine (35) is of the form $NH_2RNH_2$ in which R is any saturated or unsaturated, branched, unbranched or aromatic carbon based radical. Examples of amines that may be used in this embodiment include EDA, DETA, TETA, TEPA, MXDA, and DMAPA. The reactants may be combined in any appropriate reactor with agitation and a temperature control mechanism, such as, for example, a thermocouple device. The reactants are mixed at a temperature of between about 70° C. to about 80° C. for a period of about 4 to about 6 hours. The paraformaldehyde and the amine may be provided in excess relative to the long chain silicone cardanol dimer, although in one embodiment the mole ratio of dimer to paraformaldehyde to amine is about 1:1:1. The paraformaldehyde (13) and the amine (35) react with the long chain silicone cardanol dimer (33) to form an amine cardanol dimer curing agent (36).

The anti-fouling coating is made by mixing one or more of the epoxy components described above with one or more of the curing agents described above. Typically, the proportion of epoxy component to curing agent will be between about 0.6 to 1.8 amine functional equivalents to epoxy functional equivalents, preferably about 0.8 to 1.5 functional equivalents and more preferably between about 0.9 to 1.2 functional equivalents. In a preferred embodiment, the anti-fouling coating comprises the cardanol silane dimer epoxy (28) combined with the dimethylaminopropylaminomethyl cardanol silane dimer curing agent (15). In this embodiment, the proportion of the cardanol silane dimer epoxy (28) to dimethylaminopropylaminomethyl cardanol silane dimer curing agent (15) between about 51% to 49%.

After the epoxy component and the curing agent are combined, the anti-fouling coating is applied to a surface using standard methods known to those skilled in the art. Prior to application of the anti-fouling coating, the surface to be coated is cleaned and prepared using standard methods known to those skilled in the art. The coating may be applied to the prepared surface by brush, troweling, roller or spray applicator. The coating may be applied directly to the substrate or may be part of a multicoat system to protect the marine structure.

The anti-fouling coating is typically applied to achieve a thickness after curing of between about 25 microns to 1000 microns, preferably between about 100 microns to 500 microns. Curing time will depend upon the epoxy component and curing agent used. Typically, the curing time will be 6 to 48 hours.

Any of the cardanol dimers described above may also be used in silicone cardanol dimer based phenolic resins or to form friction particles. Friction particles typically have a resilient nature which provides cushioning in certain applications such as in brake pads and linings. Friction particles may decompose at elevated temperatures on the surface of a friction face, such as the surface of a brake lining, which can control wear and prevent excessive temperatures from developing. The friction particles may be used in phenolic binder resins resins used in brake pads. Friction particles formed using the cardanol dimers described above have better performance characteristics than friction particles formed using other silicone based materials. The friction particles formed from the cardanol dimers of the present invention exhibit reduced weight loss measured by thermogravimetric analysis, improved heat resistance and better thermal shock characteristics.

The cardanol dimers described above may also be used in phenolic resins where phenol is used in an electrophilic addition reaction.

The following examples are provided to provide additional description of the synthesis of certain embodiments of the claimed inventions. These are exemplary only, and are not intended to limit the invention in any aspect.

EXAMPLE 1

Synthesis of Acetate Substituted Cardanol

Acetic anhydride and cardanol are combined in a reactor. In a laboratory setting, the reactor is typically a glass flask. A slight excess of acetic anhydride is used, typically about 20% more than the stoichiometric quantity. The reactor is heated to a temperature of between 120° C. and 125° C. and held for three hours. If desired, the progress of the reaction can be measured by FTIR. Absorption between 3200 $cm^{-1}$ and 3500 $cm^{-1}$ represents OH absorption.

After the reaction is complete, the acetate substituted cardanol is purified by vacuum distillation. Acetic anhydride has a boiling point of 138-140° C., and acetic acid has a boiling point of 117-118° C. Both of these compounds are easily removed by vacuum distillation. After the unreacted acetic anhydride and the acetic acid by-product are removed, the acetate substituted cardanol is purified using vacuum distillation at a vacuum of 3 to 5 mm Hg and a temperature of between 240° C. and 275° C.

EXAMPLE 2

Hydrosilylation of Acetate Substituted Cardanol

The acetate substituted cardanol of example 1 and TMDS are mixed in a reactor at a mole ratio of 6:1. Speier's catalyst is added to achieve a level of 2000 ppm based upon the quantity of TMDS used. The reactor is heated to a temperature of 70° C. and held for two hours. The temperature is then increased to 80° C. and held for two hours. The temperature is then increased again to 100° C. and held for two hours. The temperature is then raised to 120° C. and held until the TMDS is no longer observed by FTIR. TMDS has a characteristic peak at 2120 $cm^{-1}$. In one run, the reaction was complete in about 10 hours.

EXAMPLE 3

Hydrolysis of Acetate Substituted Cardanol Dimer to Produce a High Viscosity Dimer The acetate group on the dimer of Example 2 is removed by hydrolysis using $HCl/H_2O$. For every 500 g of acetate substituted cardanol in the reactor, the following are added: 40 g of 37.5% HCl, 80 g of deionized water and 80 g of isopropyl alcohol. The temperature of the reactor is raised to 80° C. and held for 4 hours.

After four hours the HCl, water and isopropyl alcohol are removed by vacuum distillation of 200° C. and 5 mm Hg. The vacuum distillation is continued at 275° C. and 3 mm Hg to remove all free Cardanol. The material remaining in the reactor is a high viscosity cardanol dimer. The viscosity of the material produced in this example was about 9200 cP at 25° C., and the material had an iodine number of about 187.

EXAMPLE 4

Hydrolysis of Acetate Substituted Cardanol Dimer to Produce a Low Viscosity Dimer The acetate group on the dimer of Example 2 is removed by hydrolysis using $HCl/H_2O$. For every 500 g of acetate substituted cardanol in the reactor, the following are added: 40 g of 37.5% HCl, 80 g of deionized water, and 80 g of isopropyl alcohol. The reactor is heated to 80° C. and held at that temperature for 4 hours. The contents are then allowed to cool to room temperature.

The contents of the reactor are transferred to a separation funnel and allowed to settle to separate the aqueous and organic phases. The bottom aqueous phase is drained. The organic phase is washed twice with a 15% Brine solution, and the bottom aqueous phase is drained.

Following washing, the material is returned to the flask and vacuum distilled at 200° C. and 5 mm Hg to remove the solvent. The vacuum distillation is continued at 270° C. and 3 mm Hg to remove free Cardanol. The remaining material is a low viscosity cardanol dimer. The dimer has a viscosity of 280 cP at 25° C. and an iodine number of 154.

EXAMPLE 5

Synthesis of High Silicone Content (45%) Curing Agents from the Low and High Viscosity Dimers The following reagents are used in the amounts shown to synthesize curing agents from the high and low viscosity dimers:

TABLE 1

Formulation of the high silicone content curing agent

|   |   | Mole | Weight | Factor | Actual |
|---|---|---|---|---|---|
| A | Si-Dimers | 734.3 | 1 | 734.3 | 1/6 | 122.4 |
| B | DMAPA | 102.18 | 4.2 | 429.2 | 1/6 | 71.5 |
| C | Paraformaldehyde 91% | 30 | 4.2 | 138.6 | 1/6 | 23.1 |
| D | Aminopropyl-siloxane | 25000 | 0.033 | 824.7 | 1/6 | 137.45 |

The Si-dimers (component A) may be either the high viscosity dimer of example 3 or the low viscosity dimer of example 4 above. Components A, B, C and D are combined in the proportions set forth in Table 1 in a reactor equipped with agitation, thermocouple temperature control, and condenser. For this example, a 500 ml four neck flask was used. After the components are combined, the temperature is raised to about 75° C. and held for 4 hours. Vaccuum distillation is used at about 75° C. and 10 mm Hg to remove water. The resulting curing agent has the properties listed in Table 2 using either a low viscosity dimer or a high viscosity dimer.

TABLE 2

Analytical results for the high silicone content curing agents from low and high viscosity dimers

| LX-5335 | From the low viscosity dimers | From the high viscosity dimers |
|---|---|---|
| Visc@25 | 10240 | 16850 |
| Amine value | 200 | 190 |
| V. Loss | 3.5 | 2.3 |
| Gel time | 59.1 | 50.8 |

EXAMPLE 6

Epoxy Resin Made from the Low and High Viscosity Dimers

The following reagents are used in the amounts shown to synthesize the epoxy from the high and low viscosity dimers:

TABLE 3

Formulation for the synthesis of epoxy resin from the silicone dimer

| | | FW | Ratio | Weight | Factor | Final Charge |
|---|---|---|---|---|---|---|
| A | Si-dimers | 734.3 | 1 | 734.3 | 0.2043 | 150 |
| B | Epichlorohydrin | 92.5 | 7.6 | 703 | 0.2043 | 144 |
| C | IPA | 60 | 9.47 | 568 | 0.2043 | 95 |
| D | DI water | 18 | 6.4 | 115 | 0.2043 | 25 |
| E | NaOH (50%) | 40 | 3 | 240 | 0.2043 | 49 |
| F | DI water | 18 | 38.76 | 698 | 0.2043 | 143 |

The Si-dimers (component A) may be either the high viscosity dimer of example 3 or the low viscosity dimer of example 4 above. Components A, B, C and D are combined in the proportions set forth in Table 1 in a reactor equipped with agitation, thermocouple temperature control, a funnel and a condenser. For this example, a 1 liter four neck flask was used. After components A, B, C and D are added to the flask, they are mixed for about 20 minutes. The caustic is then added slowly to the flask through the funnel over a period of about 30 minutes. Temperature is controlled below 65° C. using a cooling water bath.

After the caustic is added, the temperature is held at 65° C. for about 4 hours. The DI water is then added through the addition funnel, and the contents of the flask are held at 65° C. and agitated for 30 minutes. The solution is transferred from the flask to a separation funnel and allowed to separate until there are clear aqueous and organic layers. This takes about 30 minutes in the laboratory. After separation, the bottom aqueous layer is drained.

The top organic layer is transferred to a clean flask. Excess solvent and free epichlorohydrin is removed by vacuum distillation at about 125° C. at 5 mm Hg. The resulting epoxy product has the following characteristics:

TABLE 4

Analytical results for the silicone dimers

| LX-5333 | From the High Viscosity Dimers | From the Low viscosity dimers |
|---|---|---|
| Visc@25 | 1400 | 370 |
| EEW | 524 | 502 |
| V. Loss | 1.3 | 0.4 |
| Hydrolizable Cl % | 0.3 | 0.8 |

EXAMPLE 7

Process for Production of Silicone Dimer Based Friction Particles

Friction particles may be made using any of the silicone cardanol dimers discussed above. In this Example, friction particles were made using cardanol dimers prepared by the method of Example 1 above with n=1. The particles may be made by blending about 50 grams of silicone dimers with 5 grams of hexamethylene tetramine in an appropriate container. The mixture is cured in an over at 180° C. for about 4 hours. The material is cooled to room temperature, broken into small pieces and ground into a fine powder. Friction particles prepared in this manner may have the following properties.

TABLE 5

Analytical properties of the Si-dimers based friction particles.

| Brown Particles | From high visc Si-dimer | From low visc Si-dimer |
|---|---|---|
| Acetone extraction | 1.3 | 0.3 |
| 370 C. V. Loss | 15.8 | 16.2 |
| Acetone Extraction After 370 C. V. Loss | 2.6 | 2.9 |
| pH | 7.35 | 6.78 |
| Ash | 1.6 | 1.7 |

EXAMPLE 8

Novolacs Phenolic Resins from Silicone Dimers

The following reagents were used in the amounts shown to produce a phenolic resin from the long chain silicone cardanol dimers described above. In this example, long chain silicone dimers with n=5 were used. The materials used to prepare the phenolic resin were as follows:

| | Description | MW | Moles Ratio | Mass | Factor | Actual charge |
|---|---|---|---|---|---|---|
| A | Si-Dimers | 734 | 1 | 734 | 0.1635 | 120 g |
| B | Paraformaldehyde | 33 | 0.75 | 24.75 | 0.1635 | 4.04 g |
| C | Oxalic Acid | 90.03 | 0.01359 | 1.223 | 0.1635 | 0.2 g |

In this example, 120 g of the Si dimer was combined in a 500 ml flask with 4.04 g of paraformaldehyde and mixed for about 20 minutes. Oxalic acid was then added to the flask and the temperature increased to 90° C.-100° C. and held at temperature for about 4 hours. The mixture was then cooled to room temperature. The phenolic resin produced by this process had a viscosity at 25° C. of about 2560 cP.

It should be understood that the results provided in these examples are for the products produced in the manner described, and that these results are not intended to limit the scope of the invention in any way, and they are exemplary only. While specific embodiments of the present invention have been described above, one skilled in the art will recognize that numerous variations or changes may be made to the invention described above without departing from the scope of the invention as recited in the appended claims. Accordingly, the foregoing detailed description of specific embodiments of the invention is intended to describe the invention in an exemplary, rather than a limiting, sense.

We claim:

1. A compound for use as an epoxy having a formula selected from the group consisting of:

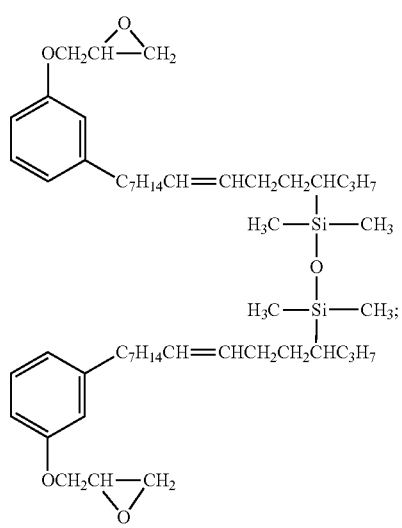
(I)

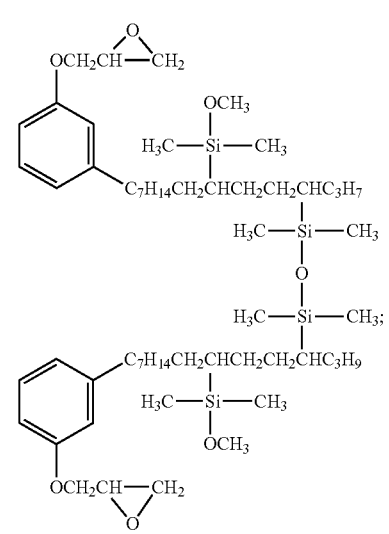
(II)

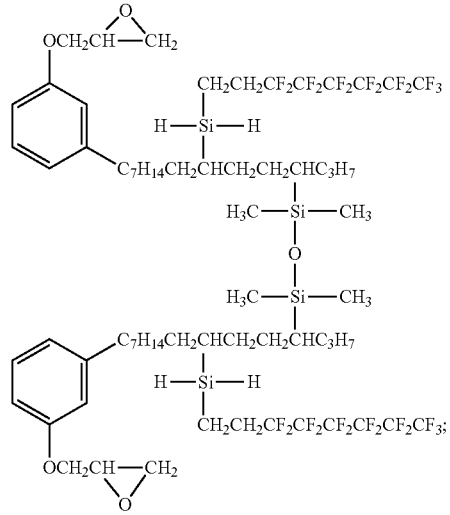
(III)

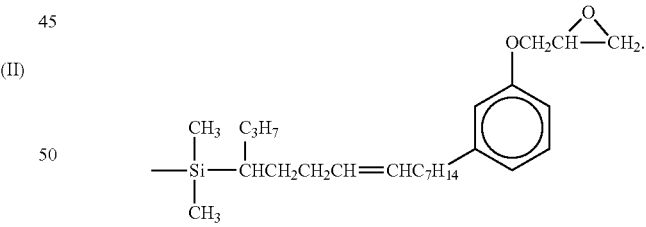
(IV)

2. An anti-fouling epoxy coating for marine surfaces comprising:
    (a) an epoxy resin comprising a silane crosslinked dimer of cardanol; and
    (b) a curing agent.

3. The anti-fouling epoxy coating of claim 2, wherein the epoxy resin is selected from the group consisting of the compounds of claim 1 having formulas I, II, III and IV.

4. The anti-fouling epoxy coating of claim 3, wherein the curing agent is selected from the group consisting of:

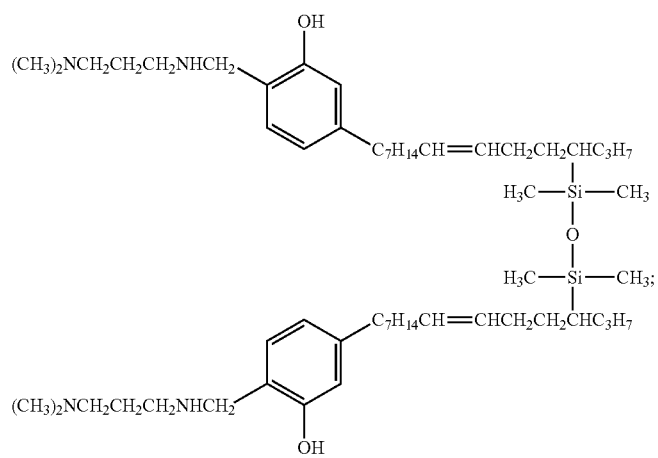
(V)
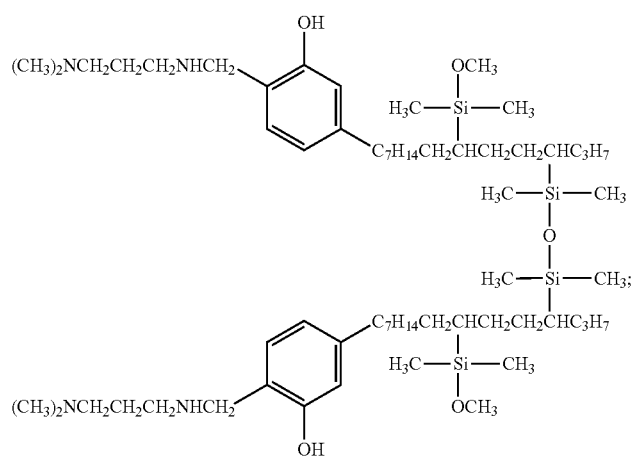
(VI)
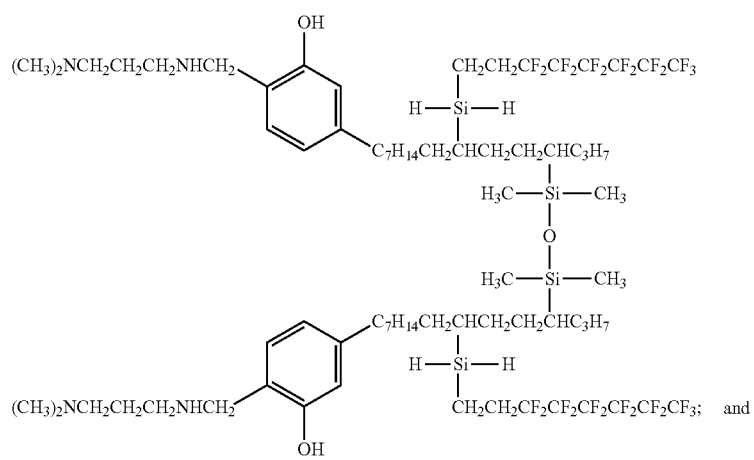
(VII)
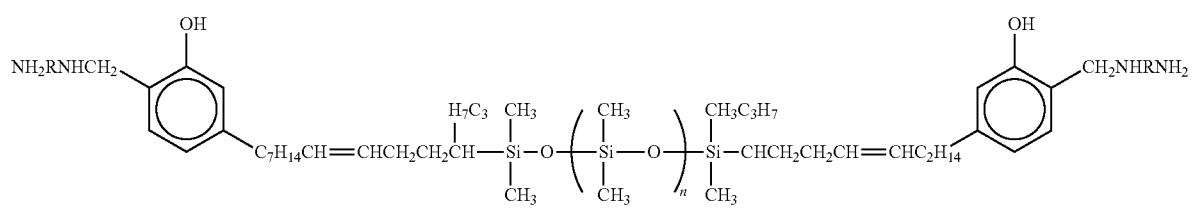
(VIII)

where n is between 5 and 200, and R is any saturated, unsaturated, branched, unbranched or aromatic carbon.

5. The anti-fouling epoxy coating of claim 3, wherein the curing agent is a functionalized cardanol selected from the group consisting of:

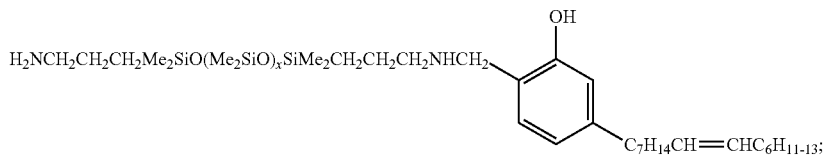
(IX)

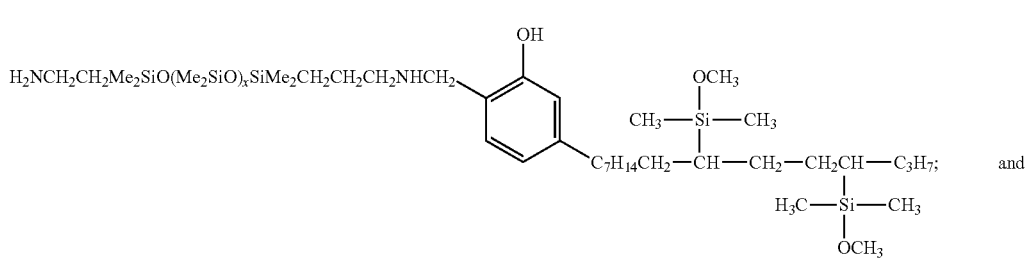
(X)

and

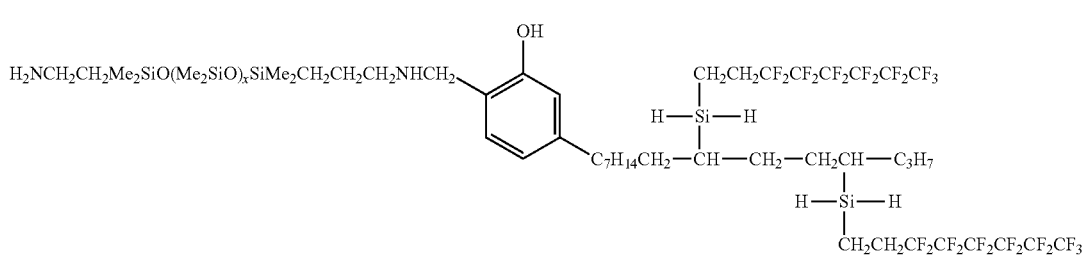
(XI)

wherein x is 9, 13, 33 or 66.

6. A process for producing a cardanol dimer based epoxy comprising the steps of:
   (a) combining cardanol and acetic anhydride in a reactor and maintaining the reactor at a temperature of between about 120° C. to 125° C. for a period of between about 3 and 4 hours;
   (b) combining the reaction product from step (a) with tetramethyldisiloxane and a catalyst in a reactor and maintaining the temperature at between about 120° C. and about 160° C. for a period of about 20 hours;
   (c) hydrolizing the reaction product from step (b) with an acid solution to produce a silane crosslinked cardanol dimer;
   (d) combining the product from step (c) with epichlorohydrin and a caustic soda solution in a reactor and maintaining the temperature between about 65° C. and about 70° C. for a period of about 3 to about 4 hours.

7. The process of claim 6, wherein the mole ratio of cardanol to acetic anhydride in step (a) is about 1:1.23.

8. The process of claim 7, wherein the mole ratio of the reaction product from step (a) to tetramethyldisiloxane is about 1:6.

9. The process of claim 8, wherein the mole ratio of the product of step (c) to epichlorohydrin is about 1:6.

10. The process of claim 9, wherein the caustic soda solution is a 50% caustic soda solution.

11. The process of claim 6, further comprising prior to step (c) the following steps:
    (i) combining the reaction product from step (b) with dimethylmethoxysilane in a reactor in the presence of a catalyst; and
    (ii) maintaining the reactor at a temperature of between about 120° C. and 160° C. for a period of about 20 hours.

12. The process of claim 11, wherein the catalyst is chloroplatinic acid hydride.

13. The process of claim 6, further comprising prior to step (c) the following steps:
    (i) combining the reaction product from step (b) with (tridecafluoro-1, 1, 2, 2tetrahydrooctyl)silane in a reactor in the presence of a catalyst; and
    (ii) maintaining the reactor at a temperature of between about 120° C. and 160° C. for a period of about 20 hours.

14. The process of claim 13, wherein the catalyst is chloroplatinic acid hydride.

* * * * *